(12) United States Patent
Bi et al.

(10) Patent No.: US 7,173,042 B2
(45) Date of Patent: Feb. 6, 2007

(54) QUINOLINE INHIBITORS OF CGMP PHOSPHODIESTERASE

(75) Inventors: Yingzhi Bi, Plainsboro, NJ (US); Guixue Yu, Lawrenceville, NJ (US); David P. Rotella, Newtown, PA (US); John E. Macor, Guilford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 93 days.

(21) Appl. No.: 11/018,968

(22) Filed: Dec. 21, 2004

(65) Prior Publication Data

US 2005/0113358 A1 May 26, 2005

Related U.S. Application Data

(62) Division of application No. 10/412,969, filed on Apr. 14, 2003, now Pat. No. 6,835,737, which is a division of application No. 09/933,066, filed on Aug. 20, 2001, now Pat. No. 6,576,644.

(60) Provisional application No. 60/230,267, filed on Sep. 6, 2000.

(51) Int. Cl.
*C07D 215/42* (2006.01)
*A61K 31/4706* (2006.01)

(52) U.S. Cl. ...................................... 514/313; 546/159
(58) Field of Classification Search ................ 546/159; 514/313
See application file for complete search history.

(56) References Cited

U.S. PATENT DOCUMENTS

| | | |
|---|---|---|
| 3,362,954 A | 1/1968 | Surrey et al. |
| 4,343,804 A | 8/1982 | Munson, Jr. et al. |
| 4,840,972 A | 6/1989 | Effland et al. |
| 5,296,484 A | 3/1994 | Coghlan et al. |
| 5,482,941 A | 1/1996 | Terrett |
| 5,488,055 A | 1/1996 | Kumar et al. |
| 5,576,322 A | 11/1996 | Takase et al. |
| 5,716,993 A | 2/1998 | Ozaki et al. |
| 6,002,008 A | 12/1999 | Wissner et al. |
| 6,087,368 A | 7/2000 | Macor et al. |
| 6,316,438 B1 | 11/2001 | Yu et al. |
| 2005/0113358 A1 | 5/2005 | Bi et al. |

FOREIGN PATENT DOCUMENTS

| | | |
|---|---|---|
| EP | 0336544 | 10/1989 |
| EP | 0480052 A1 | 4/1992 |
| FR | 2258855 | 8/1975 |
| WO | WO94/22855 | 10/1994 |
| WO | WO96/05176 | 2/1996 |
| WO | WO98/07430 | 2/1998 |
| WO | WO98/08848 | 3/1998 |
| WO | WO98/16514 | 4/1998 |
| WO | WO98/47874 | 10/1998 |
| WO | WO99/43674 | 9/1999 |
| WO | WO00/09506 | 2/2000 |
| WO | WO01/21642 | 3/2001 |
| WO | WO01/68186 | 9/2001 |

OTHER PUBLICATIONS

Savini et al., II Farmaco, 48 (6) pp. 805-825 (1993).
Eggert et al., Arch. Pharm. (Weinheim) 323 pp. 611-617 (1990).
Marecki et al., American Pharmaceutical Asso., Journal of Pharmaceutical Sciences, vol. 73, No. 8, pp. 1141-1143 (1984).
Jain et al., J. of Medicinal Chemistry, American Chemical Soc., vol. 11, No. 1 pp. 87-92 (1968).
Wright et al., J. of Medicinal Chemistry, American Chemical Soc., vol. 14, No. 11 pp. 1060-1066 (1971).
Terrett et al., Bioorganic & Medicinal Chemistry Letters, vol. 6, No. 15, pp. 1819-1824 (1996).
Elworthy et al., J. Med. Chem. vol. 40, pp. 2674-2687 (1997).
Ife et al., American Chemical Society, pp. 3413-3422 (1992).

*Primary Examiner*—Zinna N. Davis
(74) *Attorney, Agent, or Firm*—Joseph C. Wang; Laurelee A. Duncan

(57) ABSTRACT

Compounds of the formula (I)

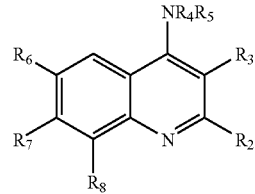

are useful as inhibitors of cGMP PDE especially Type 5.

14 Claims, No Drawings

QUINOLINE INHIBITORS OF CGMP PHOSPHODIESTERASE

RELATED INVENTIONS

This is a divisional application of U.S. Ser. No. 10/412,969, filed on Apr. 14, 2003, which is set to issue as U.S. Pat. No. 6,835,737 on Dec. 28, 2004, which is a divisional application of U.S. Ser. No. 09/933,066, filed on Aug. 20, 2001, which issued as U.S. Pat. No. 6,576,644 on Jun. 10, 2003, which claims priority from Provisional Application No. 60/230,267, filed on Sep. 6, 2000, all of which are included in their entirety by reference herein.

FIELD OF THE INVENTION

The present invention relates to quinoline compounds, to methods of using such compounds in treating cGMP-associated conditions such as erectile dysfunction, and to pharmaceutical compositions containing such compounds.

BACKGROUND OF THE INVENTION

Erectile dysfunction is the inability to obtain and maintain a penile erection sufficient for sexual intercourse or other sexual expression. A number of factors can place an individual at risk for this disorder, for example, trauma, pelvic surgery, hypercholesterolemia, ischemic heart disease, peripheral vascular disease, chronic renal failure, diabetes, the use of certain medicaments including some types of antihypertensive agents, digoxin, or the excessive use of narcotics, alcohol, tobacco, etc. Methods for treating erectile dysfunction include the use of vacuum devices and penile implants, as well as the administration of medicaments such as yohimbine, papaverine and apomorphine. Improved methods for treating this disorder are sought, however, as the aforementioned methods do not provide sufficient efficacy and/or are accompanied by drawbacks or side effects such as erosion, pain, priapism, or gastrointestinal discomfort.

A penile erection is dependent upon the presence of adequate levels of cyclic guanosine 3',5'-monophosphate (cGMP), especially in corpora cavernosa tissue. Thus, administering an inhibitor of a cGMP phosphodiesterase (cGMP PDE), particularly a selective inhibitor of cGMP PDE Type 5 (PDE 5), provides a means for achieving and maintaining an erection and therefore, for treating erectile dysfunction. See Trigo-Rocha et al., "Nitric Oxide and cGMP: Mediators of Pelvic Nerve-Stimulated Erection in Dogs," *Am. J. Physiol.*, Vol. 264 (February 1993); Bowman et al., "Cyclic GMP Mediates Neurogenic Relaxation in the Bovine Retractor Penis Muscle," *Br. J. Pharmac.*, 81, 665–674 (1984); and Rajfer et al., "Nitric Oxide as a Mediator of Relaxation of the Corpus Cavernosum in Response to Nonadrenergic, Noncholinergic Neurotransmission," *New England J. Med.*, 326, 2, 90–94 (January 1992). Sildenafil, for example, has been described as a PDE 5 inhibitor useful for treating erectile dysfunction. See *Drugs of the Future*, 22, 138–143 (1997).

Recent examples of other compounds claimed as PDE 5 inhibitors include fused pyridazine compounds (WO 96/05176 and U.S. patent application Ser. No. 09/393,833), anthranilic acid derivatives (U.S. Pat. No. 5,716,993), fused pyridopyridazine compounds (U.S. patent application Ser. No. 09/526,162), and quinazolinone compounds (U.S. Pat. No. 6,087,368).

The present invention provides compounds that are potent and selective inhibitors of cGMP PDE 5. These compounds may be employed in treating erectile dysfunction. In view of their activity, these compounds can also be used in treating other disorders responding to the inhibition of cGMP PDE, such as various cardiovascular disorders.

SUMMARY OF THE INVENTION

The present invention provides quinoline compounds of the following formula (I) or salts thereof, for use as inhibitors of cGMP PDE, especially Type 5:

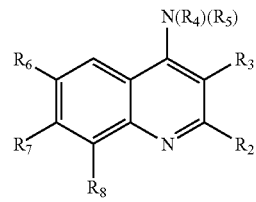

wherein:

$R_2$, $R_6$, $R_7$ and $R_8$ are independently hydrogen, halogen, alkyl, substituted alkyl, alkoxy, nitro, cyano, aryl, heteroaryl, or heterocyclo;

$R_3$ is $-(CH_2)_zY$, wherein z is 0, 1, 2, or 3;

$R_4$ and $R_5$ (i) are independently hydrogen, alkyl, substituted alkyl, cycloalykl, substituted cycloalkyl, aryl, or heteroaryl, with the proviso that $R_4$ and $R_5$ are not both hydrogen; or (ii) taken together form a heterocyclo ring;

Y is selected (i) independently from $-OR_9$, $-CO_2R_9$, $-CH(CO_2R_9)_2$, $-O(C=O)NR_{10}R_{11}$, $-NR_{10}R_{11}$, $-NR_{10}(C=O)NR_{11}R_{12}$, $-CH[(C=O)NR_{10}R_{11}]_2$, $-(C=O)NR_{10}R_{11}$, $-NR_{10}(C=O)R_{12}$, $-S(O)_mR_9$, $-SO_2NR_{10}R_{11}$, imidazole, substituted imidazole, triazole, substituted triazole, or cyano, or (ii) together with one of $R_4$ and $R_5$ to form a heterocylo ring therewith;

m is 0, 1, or 2;

$R_9$ is hydrogen, alkyl, substituted alkyl, hydroxy, alkoxy, cycloalkyl, substituted cycloalkyl, heterocyclo, aryl, heteroaryl, or pentafluorophenyl; and $R_{10}$, $R_{11}$, and $R_{12}$ (i) are independently selected from hydrogen, alkyl, substituted alkyl, alkoxy, cycloalkyl, substituted cycloalkyl, aryl, heterocyclo, and heteroaryl; or (ii) taken together wherein $R_{10}$ forms a three- to seven-membered heterocyclo ring with $R_{11}$ or $R_{12}$, or $R_{11}$ forms a three- to seven-membered heterocyclo ring with $R_{12}$.

The invention further provides pharmaceutical compositions adapted for use in treating cGMP-associated conditions comprising a pharmaceutically acceptable diluent or carrier and at least one compound of the formula (I) or salt thereof, wherein $R_2$ and $R_4$, $R_5$, $R_6$, $R_7$, $R_8$, $R_9$, $R_{10}$, $R_{11}$ and $R_{12}$ are as defined above and $R_3$ is selected from hydrogen and $-(CH_2)_zY$, with the proviso that at least one of $R_2$, $R_3$, $R_6$, $R_7$, and $R_8$ is not hydrogen. The invention further provides methods for treating cGMP-associated conditions comprising administering to a mammal in need of such treatment a therapeutically-effective amount of one or more compounds of the formula (I) or salt thereof, wherein $R_2$ and $R_4$, $R_5$, $R_6$, R7, $R_8$, $R_9$, $R_{10}$, $R_{11}$ and $R_{12}$ are as defined above and $R_3$ is selected from hydrogen and $-(CH_2)_zY$, with the proviso that at least one of $R_2$, $R_3$, $R_6$, $R_7$, and $R_8$ is not hydrogen.

DETAILED DESCRIPTION OF THE INVENTION

The following are definitions of terms used in this specification. The initial definition provided for a group or term herein applies to that group or term throughout the present specification, individually or as part of another group, unless otherwise indicated.

The term "alkyl" refers to straight or branched chain hydrocarbon groups having 1 to 12 carbon atoms, preferably 1 to 8 carbon atoms. Lower alkyl groups, that is, alkyl groups of 1 to 4 carbon atoms, are most preferred.

The term "substituted alkyl" refers to an alkyl group as defined above having one, two or three substituents selected from the group consisting of halo, amino, cyano, hydroxy, alkoxy, alkylthio, —NH(alkyl), —NH(cycloalkyl), —N(alkyl)$_2$, —C(=O)H, —CO$_2$H, —CO$_2$-alkyl, cycloalkyl, substituted cycloalkyl, aryl, heteroaryl, or heterocycle. The term "substituted alkyl" also includes an alkyl group as defined above substituted with N(substituted alkyl) or N(substituted alkyl)$_2$, or in other words, the groups (CH$_2$)$_n$NHR' and (CH$_2$)$_n$NR'R", wherein each of R' and R" comprises a substituted alkyl or R' and R" together form a heterocyclo ring.

The term "alkoxy" refers to an alkyl group as defined above bonded through an oxygen (—O—). The term "alkylthio" refers to an alkyl group as defined above bonded through a sulfur (—S—).

The term "cycloalkyl" refers to fully saturated and partially unsaturated hydrocarbon rings of 3 to 9, preferably 3 to 7, carbon atoms as well as such rings having a fused aryl ring such as indan.

The term "substituted cycloalkyl" refers to such rings having one, two or three substituents, preferably one, selected from the group consisting of alkyl, substituted alkyl, alkoxy, alkylthio, halo, hydroxy, cyano, amino, —NH(alkyl), —NH(cycloalkyl), —N(alkyl)$_2$, —CO$_2$H, —CO$_2$-lower alkyl, aryl, heterocyclo, heteroaryl, keto, =N—OH, =N—O-lower alkyl, and a five or six membered ketal, i.e. 1,3-dioxolane or 1,3-dioxane.

The term "halo" refers to chloro, bromo, fluoro and iodo.

The term "aryl" refers to phenyl, 1-naphthyl and 2-naphthyl, with phenyl being preferred. The term "aryl" includes such rings having from zero, one, two or three substituents, selected from the group consisting of alkyl, substituted alkyl, alkoxy, alkylthio, halo, hydroxy, nitro, cyano, amino, —NH(alkyl), —NH(cycloalkyl), —N(alkyl)$_2$, —CO$_2$H, —C(=O)alkyl, —CO$_2$-alkyl, cycloalkyl, substituted cycloalkyl, —(C=O)NH$_2$, —(C=O)NH(alkyl), —(C=O)NH(cycloalkyl), —(C=O)N(alkyl)$_2$, —NH—CH$_2$—CO$_2$H, —NH—CH$_2$—CO$_2$-alkyl, phenyl, benzyl, phenylethyl, phenyloxy, phenylthio, heterocyclo, and heteroaryl.

The term "heterocyclo" refers to substituted and unsubstituted non-aromatic 3 to 7 membered monocyclic groups, 7 to 11 membered bicyclic groups, and 10 to 15 membered tricyclic groups which have at least one heteroatom (O, S or N) in at least one of the rings. Each ring of the heterocyclo group containing a heteroatom can contain one or two oxygen or sulfur atoms and/or from one to four nitrogen atoms provided that the total number of heteroatoms in each ring is four or less, and further provided that the ring contains at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. The heterocyclo group may be attached at any available nitrogen or carbon atom. The heterocyclo ring may contain one, two or three substituents selected from the group consisting of halo, amino, cyano, alkyl, substituted alkyl, —NH(alkyl), —NH(cycloalkyl), —N(alkyl)$_2$, alkoxy, alkylthio, hydroxy, nitro, phenyl, benzyl, phenylethyl, phenyloxy, phenylthio, —CO$_2$H, —CO$_2$-alkyl, cycloalkyl, substituted cycloalkyl, —(C=O)NH$_2$, —(C=O)NH(alkyl), —(C=O)NH(cycloalkyl), —(C=O)N(alkyl)$_2$, —NH—CH$_2$—CO$_2$H, —NH—CH$_2$—CO$_2$-alkyl, heterocyclo, heteroaryl, keto, =N—OH, =N—O-lower alkyl, and a five or six membered ketal, i.e., 1,3-dioxolane or 1,3-dioxane.

Exemplary monocyclic groups include azetidinyl, pyrrolidinyl, oxetanyl, imidazolinyl, oxazolidinyl, isoxazolinyl, thiazolidinyl, isothiazolidinyl, tetrahydrofuranyl, piperidinyl, piperazinyl, 2-oxopiperazinyl, 2-oxopiperidinyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl.

The term "heteroaryl" refers to substituted and unsubstituted aromatic 5 or 6 membered monocyclic groups, 9 or 10 membered bicyclic groups, and 11 to 14 membered tricyclic groups which have at least one heteroatom (O, S or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain one, two or three substituents selected from the group consisting of halo, amino, cyano, alkyl, substituted alkyl, —NH(alkyl), —NH(cycloalkyl), —N(alkyl)$_2$, alkoxy, alkylthio, hydroxy, nitro, phenyl, benzyl, phenylethyl, phenyloxy, phenylthio, —CO$_2$H, —CO$_2$-alkyl, cycloalkyl, substituted cycloalkyl, —(C=O)NH$_2$, —(C=O)NH(alkyl), —(C=O)NH(cycloalkyl), —(C=O)N(alkyl)$_2$, —NH—CH$_2$—CO$_2$H, —NH—CH$_2$—CO$_2$-alkyl, heterocylco, and heteroaryl.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxaxolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridinyl, dihydroisoindolyl, tetrahydroquinolinyl and the like.

Exemplary tricyclic heteroaryl groups include carbazolyl, benzidolyl, phenanthrollinyl, acridinyl, phenanthridinyl, xanthenyl and the like.

The term "substituted imidazole" refers to an imidazole, an aryl-fused imidazole such as benzimidazole, or a heteroaryl-fused imidazole such as a pyridoimidazole which contain one or two substituents selected from the group consisting of hydrogen, alkyl, substituted alkyl, alkoxy, alkylthio, halo, hydroxy, nitro, cyano, amino, —NH(alkyl), —NH(cycloalkyl), —N(alkyl)$_2$, —CO$_2$H, —CO$_2$-alkyl, cycloalkyl, substituted cycloalkyl, —(C=O)NH$_2$, —(C=O)NH(alkyl), —(C=O)NH(cycloalkyl), —(C=O)N(alkyl)$_2$, —NH—CH$_2$—CO$_2$H, —NH—CH$_2$—CO$_2$-alkyl, phenyl, benzyl, phenylethyl, phenyloxy, phenylthio, heterocyclo, and heteroaryl.

The term "substituted triazole" refers to a triazole having at least one substituent selected from the group consisting of alkyl, substituted alkyl, alkoxy, alkylthio, halo, hydroxy, nitro, cyano, amino, —NH(alkyl), —NH(cycloalkyl), —N(alkyl)$_2$, —CO$_2$H, —CO$_2$-alkyl, cycloalkyl, substituted cycloalkyl, —(C=O)NH$_2$, —(C=O)NH(alkyl), —(C=O)NH(cycloalkyl), —(C=O)N(alkyl)$_2$, —NH—CH$_2$—CO$_2$H, —NH—CH$_2$—CO$_2$-alkyl, phenyl, benzyl, phenylethyl, phenyloxy, phenylthio, heterocyclo, and heteroaryl.

Throughout the specification, groups and substituents thereof may be chosen to provide stable moieties and compounds.

The compounds of formula I form salts which are also within the scope of this invention. Reference to a compound of the formula I herein is understood to include reference to salts thereof, unless otherwise indicated. The term "salt(s)", as employed herein, denotes acidic and/or basic salts formed with inorganic and/or organic acids and bases. In addition, when a compound of formula I contains both a basic moiety, such as, but not limited to an amine or a pyridine or imidazole ring, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds of the formula I may be formed, for example, by reacting a compound of the formula I with an amount of acid or base, such as an equivalent amount, in a medium such as one in which the salt precipitates or in an aqueous medium followed by lyophilization.

The compounds of formula I which contain a basic moiety, such as, but not limited to an amine or a pyridine or imidazole ring, may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The compounds of formula I which contain an acidic moiety, such as, but not limited to a carboxylic acid, may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines [formed with N,N-bis(dehydro-abietyl)ethylenediamine], N-methyl-D-glucamines, N-methyl-D-glucamides, t-butyl amines, and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Prodrugs and solvates of the compounds of this invention are also contemplated herein. The term "prodrug", as employed herein, denotes a compound which, upon administration to a subject, undergoes chemical conversion by metabolic or chemical processes to yield a compound of the formula I, and/or a salt and/or solvate thereof. Solvates of the compounds of formula I are preferably hydrates.

Compounds of the formula I, and salts thereof, may exist in their tautomeric form (for example, as an amide or imino ether). All such tautomeric forms are contemplated herein as part of the present invention.

All stereoisomers of the present compounds, such as those, for example, which may exist due to asymmetric carbons on the $R_2$ to $R_{12}$ substituents, including enantiomeric forms (which may exist even in the absence of asymmetric carbons) and diastereomeric forms, are contemplated and within the scope of this invention. Individual stereoisomers of the compounds of this invention may, for example, be substantially free of other isomers, or may be admixed, for example, as racemates or with all other or other selected, stereoisomers. The chiral centers of the present invention can have the S or R configuration as defined by the IUPAC 1974 Recommendations.

Methods of Preparation

The compounds of the present invention may be prepared by methods such as those illustrated in the following Schemes I to X. Starting materials are commercially available or can be readily prepared by one of ordinary skill in the art using known methods. For all of the schemes and compounds, the groups $R_2$, $R_3$, $R_4$, $R_5$, $R_6$, $R_7$, and $R_8$ are as described above for a compound of formula I, unless otherwise indicated.

Solvents, temperatures, pressures, and other reaction conditions may readily be selected by one of ordinary skill in the art. For example, in these schemes exemplary hydroxide sources may include sodium hydroxide or lithium hydroxide; an exemplary reducing reagent and inert solvent (for reducing a carboxylic acid or ester group to an alcohol) includes lithium tri-t-butoxyaluminohydride and tetrahydrofuran (THF); exemplary dehydrating/chlorinating agents include POCl$_3$, PCl$_5$, SOCl$_2$ or oxalyl chloride; exemplary leaving groups (LG) include triflate, mesylate, tosylate, or halide; and exemplary reagents (for converting a hydroxyl group to a leaving group) include trifluoromethanesulfonyl chloride, toluenesulfonyl chloride, methanesulfonyl chloride, phosphorus oxychloride, thionyl chloride, and phosphorus pentachloride. Exemplary solvents, as appropriate, may be selected from 1,2-dichlorobenzene, methylene chloride, dimethylformamide (DMF), alcohols, ethers, including diphenyl ether, tetrahydrofuran and dioxane, N,N-dimethylformamide, and acetonitrile, water, mixtures of ethers and water, and the like.

High Speed Analoging (HSA) may be employed in the preparation of compounds.

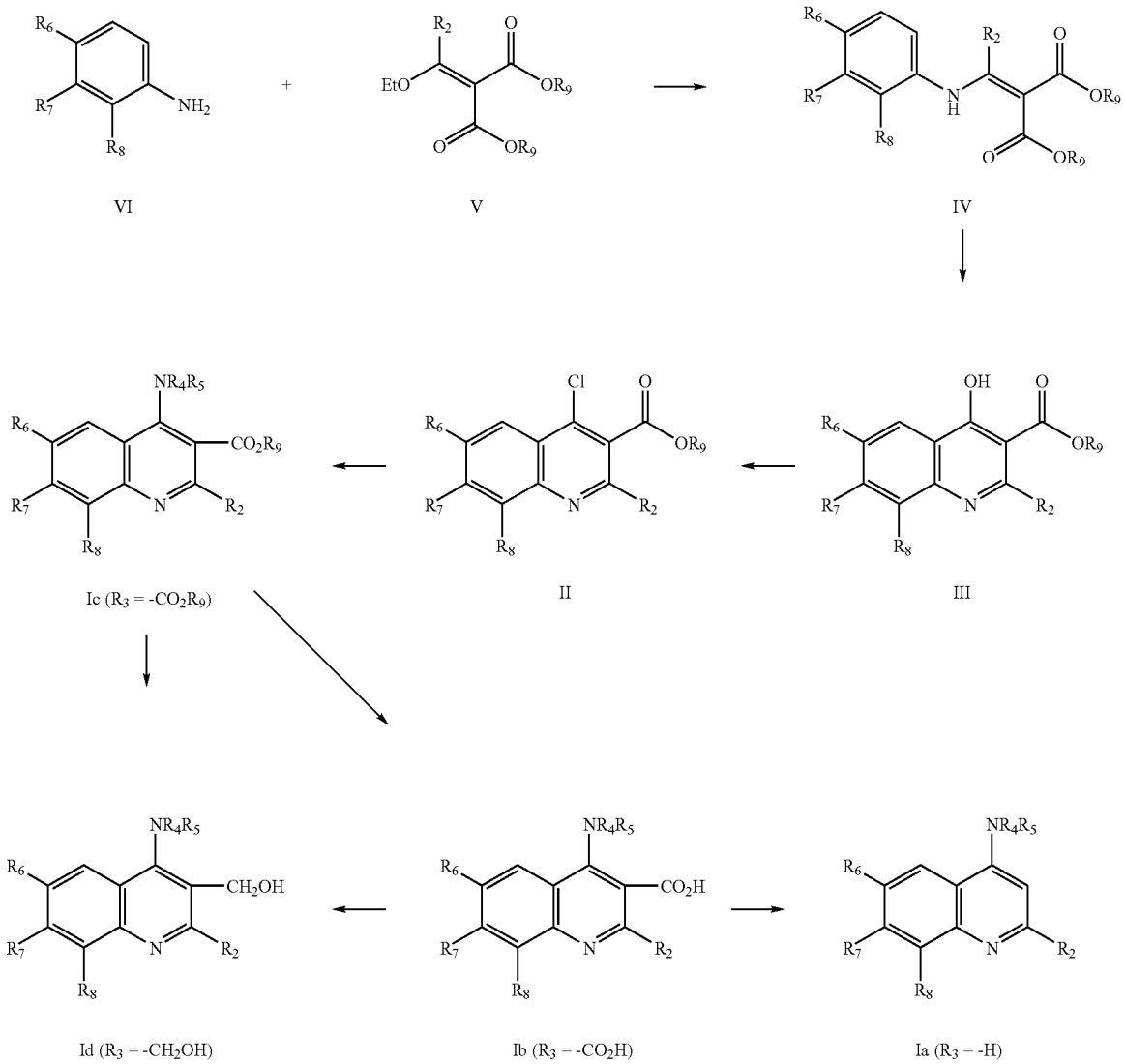

SCHEME I

Compounds of formula Ia wherein $R_3$ is hydrogen can be prepared via the decarboxylation of a compound of formula Ib in an appropriate degassed inert solvent (e.g., 1,2-dichlorobenzene and diphenyl ether) at elevated temperature.

Compounds of formula Ib wherein $R_3$ is —$CO_2H$ can be prepared by the hydrolysis of compounds of formula Ic using a hydroxide source and appropriate solvent (e.g., water, alcohols, and mixtures of ethers and water).

Compounds of formula Id wherein $R_3$ is —$CH_2OH$ can be prepared by reducing a compound of formula Ib or Ic with an appropriate reducing reagent in an inert (reaction) solvent.

Compounds of formula Ic wherein $R_3$ is —$CO_2R_9$ can be prepared by reacting compounds of formula II with an amine of the formula $NHR_4R_5$. The reaction may be performed in a solvent as appropriate, such as an alcohol, in the presence of an appropriate base, such as triethylamine, and typically under elevated temperatures.

Compounds of formula II can be prepared by reacting compounds of formula III with an appropriate dehydrating/chlorinating agent, typically under elevated temperatures.

Compounds of formula III can be prepared from compounds of formula IV via an intramolecular cyclization typically under elevated temperatures in an inert solvent, as appropriate, or in neat form.

Compounds of formula IV can be prepared by combining compounds of formula V and VI either neat or in an inert solvent as appropriate, typically under elevated temperatures.

Compounds of formula V and formula VI are either commercially available or available via methods known to one skilled in the art.

SCHEME II

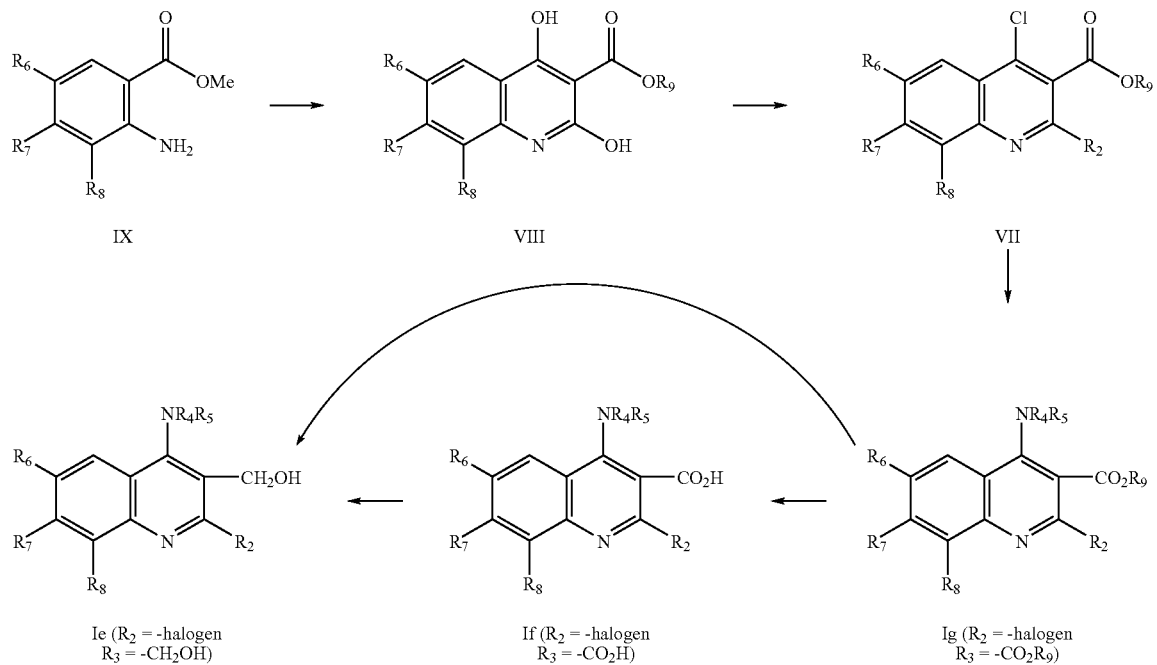

Compounds of formula Ie wherein $R_2$ is halogen and $R_3$ is —$CH_2OH$ can be prepared by reducing a compound of formula If or Ig with an appropriate reducing reagent in an inert (reaction) solvent.

Compounds of formula If wherein $R_2$ is halogen and $R_3$ is —$CO_2H$ can be prepared by the hydrolysis of compounds of formula Ig using a hydroxide source in appropriate solvent.

Compounds of formula Ig wherein $R_2$ is halogen and $R_3$ is —$CO_2R_9$ ($R_9$ is other than hydrogen) can be prepared by reacting compounds of formula VII with an amine of the formula $NHR_4R_5$ (as in Scheme I for formula Ic).

Compounds of formula VII can be prepared by reacting compounds of formula VIII with an appropriate dehydrating/chlorinating agent typically under elevated temperatures.

Compounds of formula VIII can be prepared from compounds of formula IX by a condensation with a malonate derivative using base in an appropriate solvent. Sodium alkoxides are exemplary bases and alcohols exemplary solvents.

Compounds of formula IX are either commercially available or available via methods known to one skilled in the art.

SCHEME III

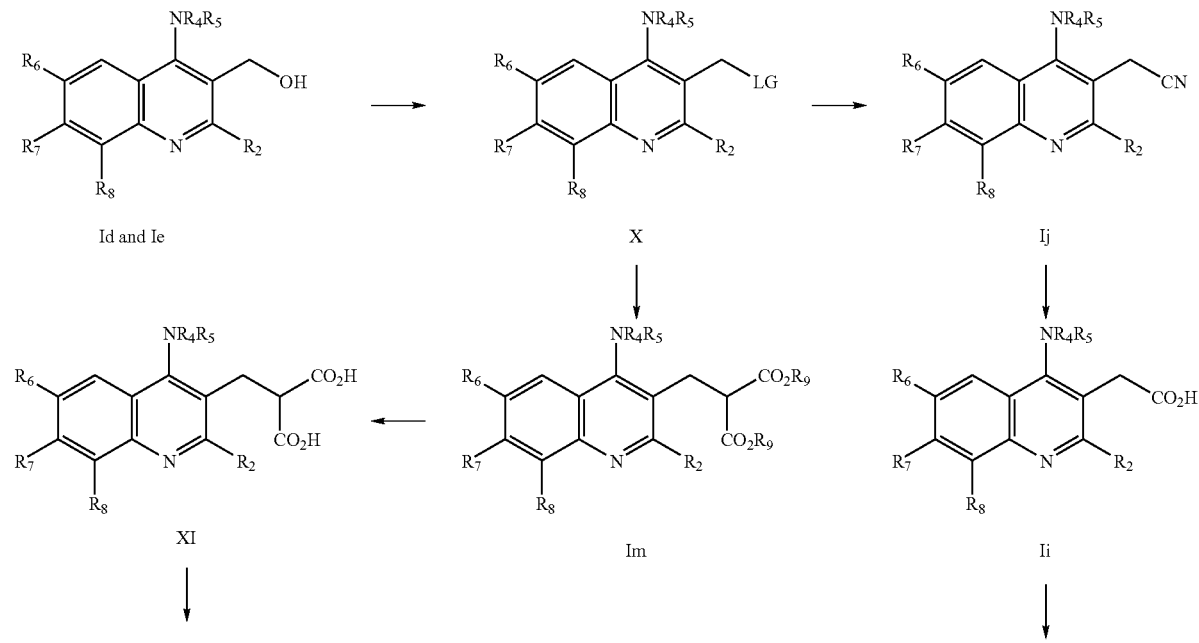

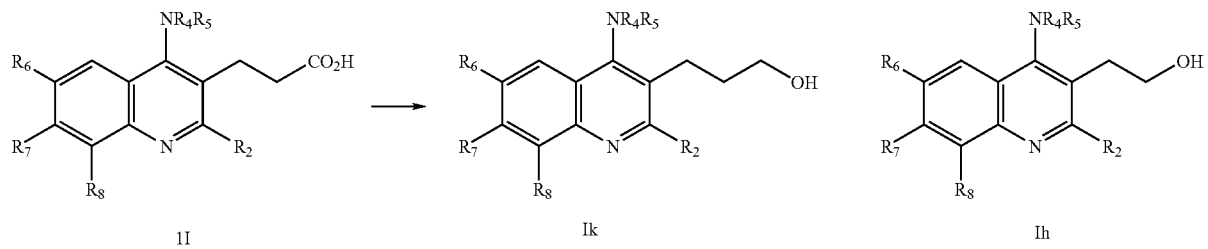

Compounds of formula Ih wherein $R_3$ is —$(CH_2)_2OH$ can be prepared by reducing a compound of formula Ii with an appropriate reducing reagent in an inert solvent.

Compounds of formula Ii wherein $R_3$ is —$CH_2CO_2H$ can be prepared by the hydrolysis of compounds of formula Ij using a hydroxide source in appropriate solvent.

Compounds of formula Ij wherein $R_3$ is —$CH_2CN$ can be prepared via the displacement of the leaving group (LG) from a compound of formula X using an appropriate nucleophile in an inert solvent (e.g., methylene chloride). Nucleophiles may include cyanides from HCN, KCN, or NaCN, or tetrabutylammonium cyanide.

Compounds of formula X can be prepared via reaction of compounds of formula Id or Ie with an appropriate reagent which converts the hydroxyl group to a leaving group (LG) in an inert solvent (e.g., methylene chloride).

Compounds of formula Id or Ie wherein $R_3$ is —$CH_2OH$, can be prepared by the methods described above in Schemes I and II.

Compounds of formula Ik wherein $R_3$ is —$(CH_2)_3OH$ can be prepared by reducing a compound of formula II with an appropriate reducing reagent in an inert solvent. Compounds of formula II can be prepared by decarboxylation of compounds of formula XI at elevated temperature in an inert solvent (e.g., DMF).

Compounds of formula XI can be prepared by the hydrolysis of compounds of formula Im using a hydroxide source and an appropriate solvent.

Compounds of formula Im wherein $R_3$ is —$CH_2CH(CO_2R_9)_2$ can be prepared via the displacement of the leaving group (LG) from a compound of formula X using an appropriate nucleophile (e.g., alkyl malonate) in an inert solvent (e.g., methylene chloride).

SCHEME IV

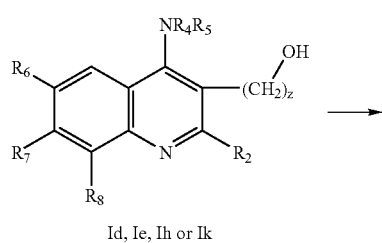

Id, Ie, Ih or Ik

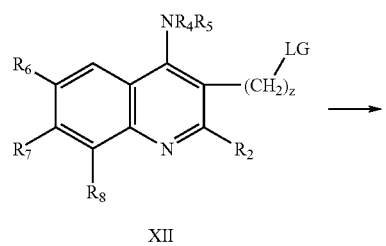

Compounds of formula In wherein $R_3$ is —$(CH_2)_zY$ can be prepared via the displacement of the leaving group (LG) from a compound of formula XI using an appropriate nucleophile in an inert solvent. Exemplary nucleophiles include alcohols of the formula $HOR_9$, amines of the formula $HNR_{10}R_{11}$, mercaptans of the formula $HSR_9$, cyanides as in Scheme III, imidazole, substituted imidazoles, triazole, and substituted triazoles.

Compounds of formula XII can be prepared via reaction of compounds of formulas Id, Ie, Ih, Ik with an appropriate reagent which converts the hydroxyl group to a leaving group (LG) in an appropriate inert solvent.

Compounds of formulas Id (z=1), Ie (z=1), Ih (z=2), Ik (z=3) can be prepared using the methods described above in Schemes I, II or III.

SCHEME V

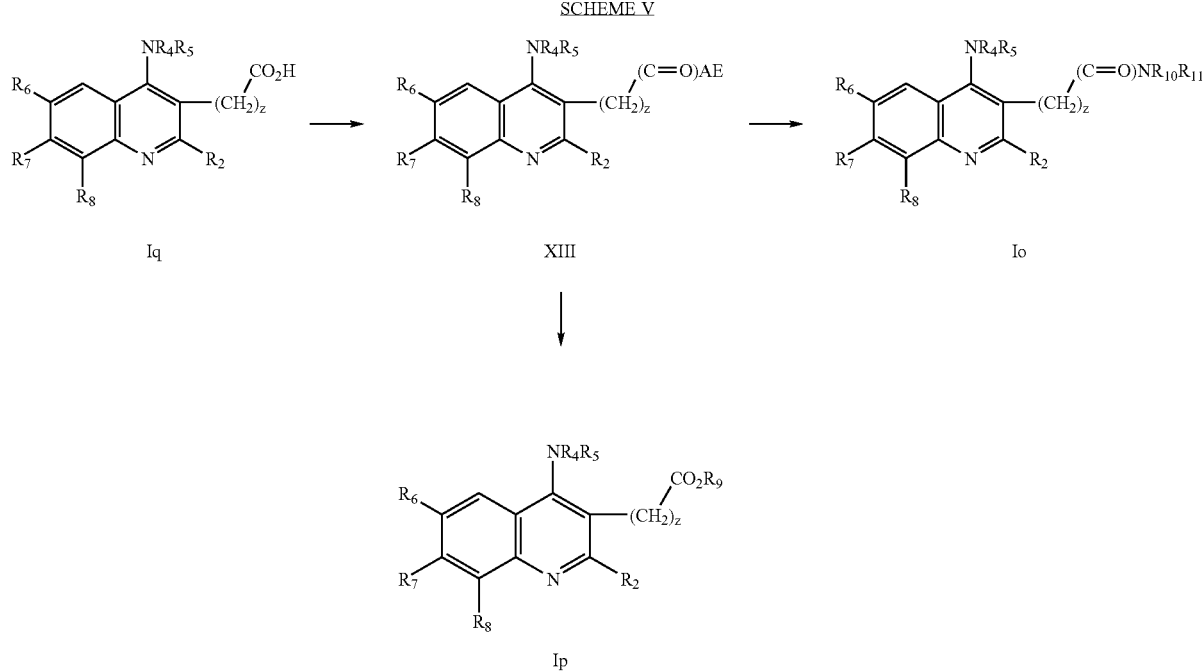

Compounds of formula Io wherein $R_3$ is —$(CH_2)_z(C=O)NR_{10}R_{11}$ can be prepared via the aminolysis of an active ester (AE) of formula XIII using an amine of the formula $NHR_{10}R_{11}$ in an inert solvent (e.g., ethers, described above, and methylene chloride).

Compounds of formula Ip wherein $R_3$ is —$(CH_2)_zCO_2R_9$ can be prepared via the esterification of a compound of formula XIII using an alcohol of the formula $HOR_9$, with the alcohol used as solvent or in an inert solvent such as ethers, described above, or methylene chloride.

Compounds of formula XIII can be prepared via the activation of the carboxylic acid in compounds of formula Iq using an appropriate carboxylic acid activating agent in an appropriate solvent. Exemplary activating agents include carbonyldiimidazole or dicyclohexyl carbodiimide and pentafluorophenol.

Compounds of formula Iq wherein $R_3$ is —$(CH_2)_zCO_2H$ can be prepared with the methods described in Schemes III and IV.

SCHEME VI

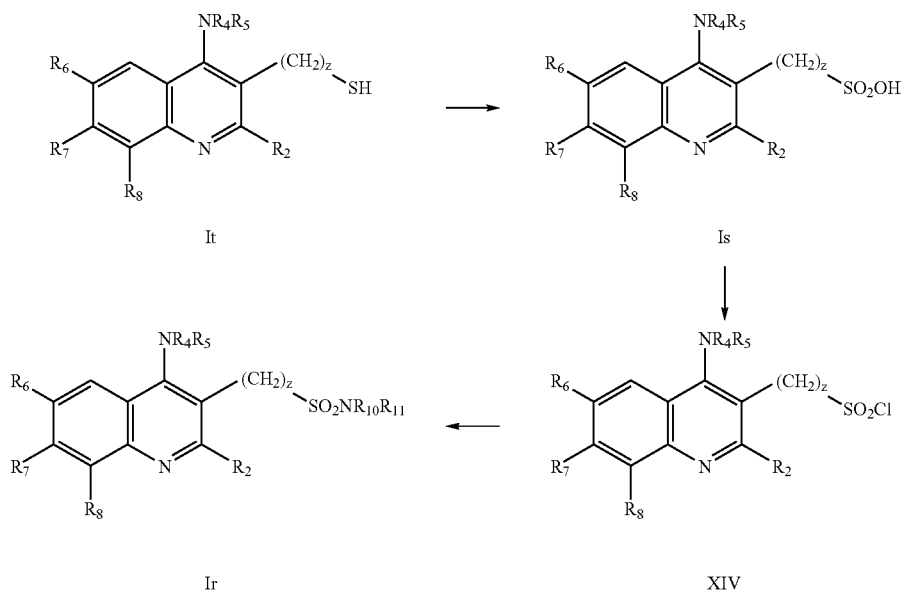

Compounds of formula Ir wherein $R_3$ is —$(CH_2)_z$ $SO_2NR_{10}R_{11}$ can be prepared via the aminolysis of a sulfonyl chloride of formula XIV using an amine of the formula $NHR_{10}R_{11}$ in an inert solvent (e.g., ethers or methylene chloride).

Compounds of formula XIV can be prepared by reacting compounds of formula Is with an appropriate dehydrating/chlorinating agent typically under elevated temperatures.

Compounds of formula Is wherein $R_3$ is —$(CH_2)_z SO_2OH$ can be prepared by oxidation of compounds of formula It.

Compounds of formula It wherein $R_3$ is —$(CH_2)_z SH$ can be prepared by the methods described above in Scheme IV.

-continued

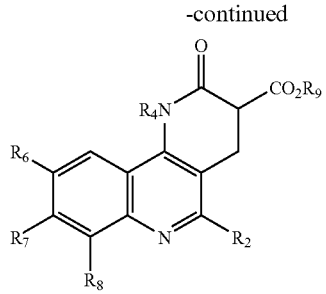

Iz

SCHEME VII

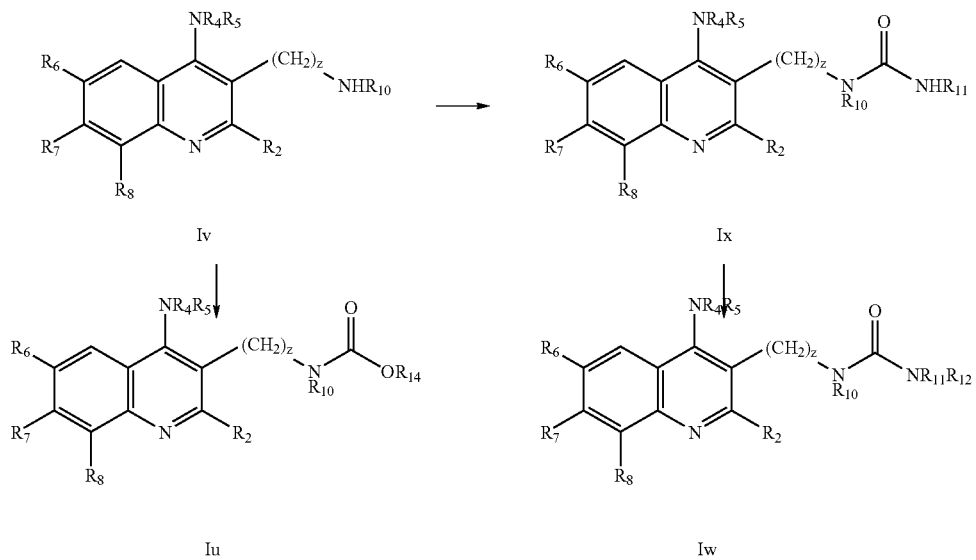

Iv

Ix

Iu

Iw

Compounds of formula Iu wherein $R_3$ is —$(CH_2)_z NR_{10}$ (C=O)$OR_{11}$ can be prepared by reacting compounds of formula Iv with a chloroformate in an inert solvent.

Compounds of formula Iw wherein $R_3$ is —$(CH_2)_z NR_{10}$ (C=O)$NR_{11}R_{12}$ can be prepared by reacting compounds of formula Ix with an alkylating agent under basic conditions in an inert solvent.

Compounds of formula Ix wherein $R_3$ is —$(CH_2)_z NR_{10}$ (C=O)$NHR_{11}$ can be prepared by reacting compounds of formula Iv with an isocynate in an inert solvent.

Compounds of formula Iv can be prepared with the methods described above in Scheme IV.

SCHEME VIII

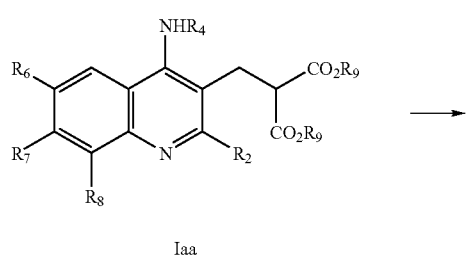

Iaa

-continued

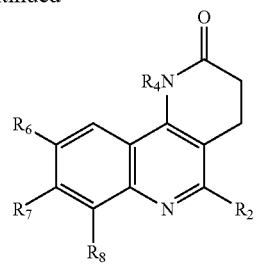

Iy

Compounds of formula Iy wherein $R_3$ and $R_5$ form a heterocyclo carboxamide ring can be prepared from compounds of formula Iz by hydrolysis and decarboxylation.

Compounds of formula Iz wherein $R_3$ and $R_5$ form a 2-carboxylate heterocyclo carboxamide ring can be prepared from compounds of formula Iaa by a base effected cyclization.

Compounds of formula Iaa wherein $R_3$ is —$CH_2CH$ $(CO_2R_9)_2$ and $R_5$ is hydrogen can be prepared with the methods described in Scheme III.

SCHEME IX

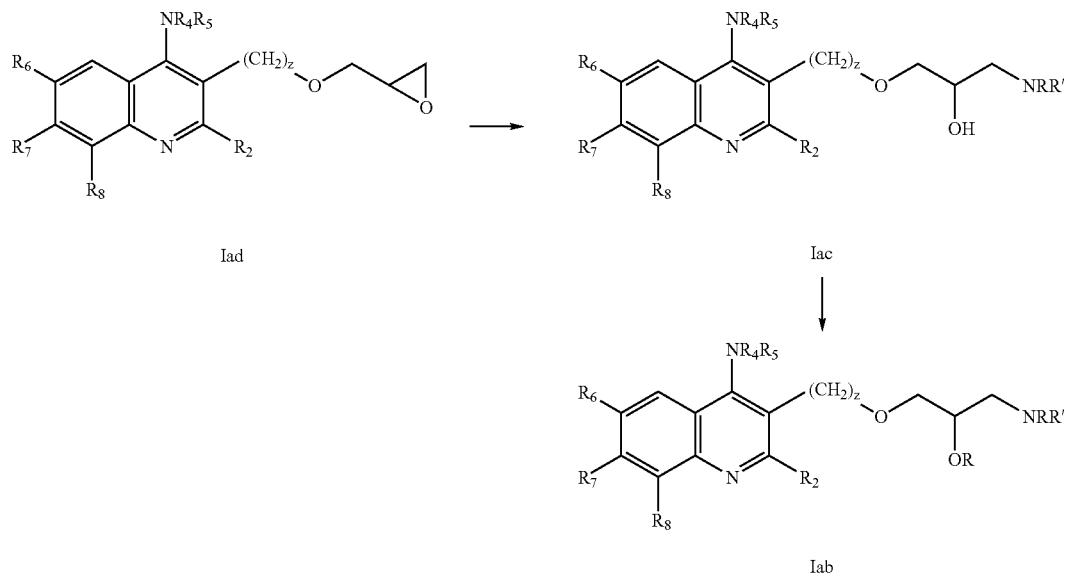

Compounds of formula Iab wherein $R_3$ is —$(CH_2)_z$ $OR_9$ $(OR_{10})NR_{11}R_{12}$ can be prepared from compounds of formula Iac by a base-effected alkylation.

Compounds of formula Iac wherein $R_3$ is —$(CH_2)_z$ $OR_9$ $(OH)NR_{11}R_{12}$ can be prepared from compounds of formula Iab by an aminolysis of the epoxide.

Compounds of formula Iad wherein $R_3$ is —$(CH_2)_z$ $OR_9NR_{10}R_{11}$ can be prepared by the method described in Scheme IV.

Compounds of formula Ia wherein $R_3$ is hydrogen can also be prepared from compounds of formula XV by a base-effected alkylation.

Compounds of formula XV can be prepared from compounds of formula XVI by a Curtius rearrangement.

Compounds of formula XVI can be prepared by reacting compounds of formula XVII with an appropriate methyl ketone.

Compounds of formula XVII are either commercially available or available via methods known to one skilled in the art.

SCHEME X

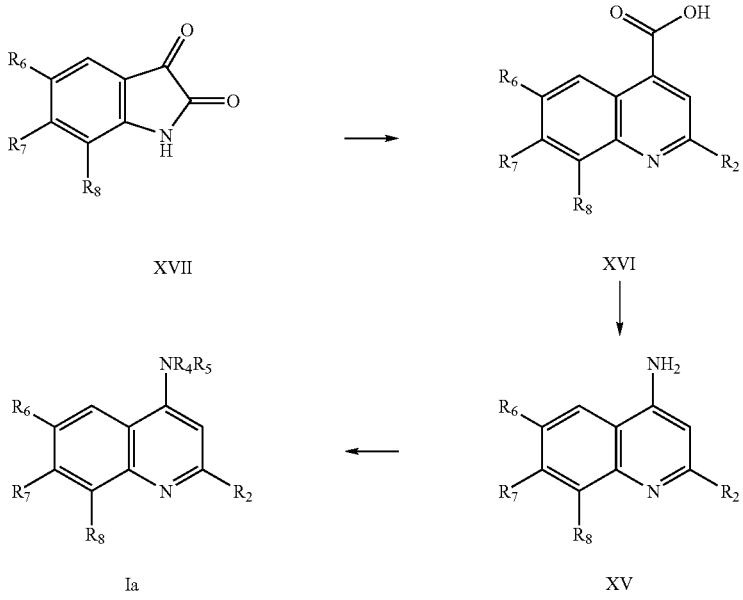

Preferred Compounds

Preferred compounds of this invention are those of formula (I) and/or pharmaceutically acceptable salts thereof having the following definitions:

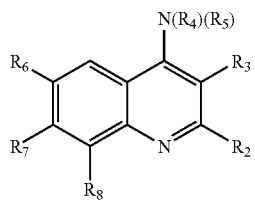

wherein,
$R_2$, $R_6$, and $R_7$ are independently hydrogen, halogen, alkyl, substituted alkyl, nitro, cyano, aryl, or heteroaryl;
$R_8$ is hydrogen, alkyl, or substituted alkyl, including —$(CH_2)_nNR_{13},R_{14}$, wherein $R_{13}$ and $R_{14}$ (i) are independently selected from hydrogen, alkyl, or substituted alkyl, or (ii) taken together form a heterocylco ring;
$R_3$ is —$(CH_2)_zY$;
$R_4$ is hydrogen, lower alkyl, or forms a heterocyclo ring with Y or $R_3$;
$R_5$ is substituted alkyl;
$R_6$ is hydrogen, halogen, trifluoromethyl, nitro, cyano, or aryl;
Y is (i) independently selected from —$OR_9$, —$CO_2R_9$, —$CH(CO_2R_9)_2$, —$O(C=O)$ $NR_{10}R_{11}$, —$NR_{10}R_{11}$, —$NR_{10}(C=O)NR_{11}R_{12}$, —$CH[(C=O)NR_{10}R_{11}]_2$, —$(C=O)NR_{10}R_{11}$, —$NR_{10}(C=O)R_{12}$, —$S(O)_mR_9$, —$SO_2NR_{10}R_{11}$, imidazole, substituted imidazole, triazole, substituted triazole, or cyano, or (ii) taken together with $R_4$ or $R_5$, forming a heterocylo ring therewith;
m is 0, 1, or 2;
n is 0, 1, 2, or 3;
z is 0, 1, 2, or 3;
$R_9$ is hydrogen, alkyl, substituted alkyl, hydroxy, alkoxy, cycloalkyl, substituted cycloalkyl, heterocyclo, aryl, heteroaryl, or pentafluorophenyl; and
$R_{10}$, $R_{11}$, and $R_{12}$ (i) are independently selected from hydrogen, alkyl, substituted alkyl, alkoxy, cycloalkyl, substituted cycloalkyl, aryl, heterocyclo, or heteroaryl; or (ii) taken together wherein $R_{10}$ with $R_{11}$ or $R_{12}$ forms a three- to seven-membered heterocyclo ring, or $R_{10}$ with $R_{12}$ forms a three- to seven-membered heterocyclo ring.

More preferred are the compounds of formula (I), above, and/or pharmaceutically acceptable salts thereof, wherein
$R_2$ is hydrogen, halogen, lower alkyl, or pyridine;
$R_3$ is —$(CH_2)_zY$;
$R_4$ is hydrogen, methyl, or forms a heterocyclo ring with Y or $R_3$;
$R_5$ is substituted alkyl, wherein said substituted alkyl comprises an aryl, cycloalkyl, or heteroaryl substituent;
$R_6$ is hydrogen, halogen, trifluoromethyl, or cyano;
$R_7$ is hydrogen or trifluoromethyl;
$R_8$ is hydrogen, alkyl, substituted alkyl, or —$(CH_2)_nNR_{13}$, $R_{14}$, wherein $R_{13}$ and $R_{14}$ (i) are independently selected from hydrogen, alkyl, or substituted alkyl, or (ii) together form a heterocylco ring;
Y is (i) —$OR_9$, —$CO_2R_9$, —$CH(CO_2R_9)_2$, —$OR_9NR_{10}R_{11}$, —$NR_{10}R_{11}$, —$(C=O)NR_{10}R_{11}$, —$NR_{10}(C=O)R_{12}$, or (ii) together with $R_4$ forms a heterocylo ring;
n is 0, 1, 2, or 3;
z is 0, 1, 2, or 3;
$R_9$ is hydrogen, alkyl, substituted alkyl, alkoxy, heterocyclo, or pentafluorophenyl;
$R_{10}$ and $R_{11}$ are (i) independently selected from hydrogen, alkyl, substituted alkyl, alkoxy, cycloalkyl, substituted cycloalkyl, aryl, heterocyclo, or heteroaryl; or (ii) taken together wherein $R_{10}$ and $R_{11}$ forms a three- to seven-membered heterocyclo ring; and
$R_{12}$ is aryl, cycloalkyl, or heteroaryl.

Advantageously, $R_5$ comprises cycloalkyl or an alkyl substituted with aryl. When $R_5$ is an alkyl substituted with an aryl, advantageously the aryl has one to two substituents wherein at least one of the substituents is selected from halogen (e.g., chloro, bromo, fluoro), alkoxy (e.g., methoxy), or a lower alkyl. Advantageously, when $R_9$ comprises a heterocyclo ring with a nitrogen heteroatom, said nitrogen heteroatom has a substituent $X_1$ selected from lower alkyl, substituted alkyl, and cycloalkyl. When $R_4$ and $R_3$ (or Y) form a heterocyclo ring, said ring advantageously is unsubstituted or has at least one substituent $X_2$ comprising $CO_2$ (alkyl).

Most preferred are the compounds of formula (I) and/or pharmaceutically acceptable salts thereof, wherein:
$R_2$ is hydrogen or chloro;
$R_3$ is —$(CH_2)_zY$, wherein z is 0, 1, 2, or 3;
$R_4$ is hydrogen;
$R_5$ is 3-chloro-4-methoxyphenylmethyl;
$R_6$ is cyano;
$R_7$ is hydrogen;
$R_8$ is hydrogen, alkyl, or substituted alkyl;
Y is —$OR_9$, —$NR_{10}R_{11}$, —$CO_2R_9$, or —$(C=O)NR_{10}R_{11}$;
$R_9$ is hydrogen, alkyl, or substituted alkyl; and
$R_{10}$ and $R_{11}$ (i) are each independently hydrogen, alkyl, substituted alkyl, aryl, heterocyclo, or heteroaryl; or (ii) together form a five- to seven-membered heterocyclo ring.

Preferred Pharmaceutical Compositions for Treating cGMP-Associated Conditions

Preferred pharmaceutical compositions of this invention are those compositions adapted for use in treating cGMP-associated conditions comprising a pharmaceutically acceptable diluent or carrier and at least one compound of the formula (I) and/or pharmaceutically acceptable salts thereof:

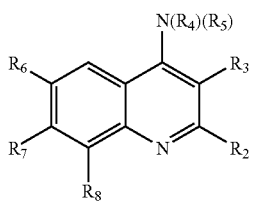

wherein,
$R_2$, $R_6$, and $R_7$ are independently hydrogen, halogen, alkyl, substituted alkyl, nitro, cyano, aryl, or heteroaryl;
$R_8$ is hydrogen, alkyl, substituted alkyl, or —$(CH_2)_nNR_{13}$, $R_{14}$, wherein $R_{13}$ and $R_{14}$ (i) are independently selected from hydrogen, alkyl, or substituted alkyl, or (ii) taken together form a heterocylco ring;
$R_3$ is hydrogen or —$(CH_2)_zY$;
$R_4$ is hydrogen, lower alkyl, or forms a heterocyclo ring with Y or $R_3$;

$R_5$ is substituted alkyl;

$R_6$ is hydrogen, halogen, trifluoromethyl, nitro, cyano or aryl;

Y is selected (i) independently from —$OR_9$, —$CO_2R_9$, —$CH(CO_2R_9)_2$, —$O(C=O)$ $NR_{10}R_{11}$, —$NR_{10}R_{11}$, —$NR_{10}(C=O)NR_{11}R_{12}$, —$CH[(C=O)NR_{10}R_{11}]_2$, —$(C=O)NR_{10}R_{11}$, —$NR_{10}(C=O)R_{12}$, —$S(O)_mR_9$, —$SO_2NR_{10}R_{11}$, imidazole, substituted imidazole, triazole, substituted triazole, or cyano, or (ii) together with $R_4$ or $R_5$, forming a heterocylo ring therewith;

m is 0, 1, or 2;

n is 0, 1, 2, or 3;

z is 0, 1, 2, or 3;

$R_9$ is hydrogen, alkyl, substituted alkyl, hydroxy, alkoxy, cycloalkyl, substituted cycloalkyl, heterocyclo, aryl, heteroaryl, or pentafluorophenyl; and $R_{10}$, $R_{11}$, and $R_{12}$ (i) are independently selected from hydrogen, alkyl, substituted alkyl, alkoxy, cycloalkyl, substituted cycloalkyl, aryl, heterocyclo, or heteroaryl; or (ii) taken together wherein $R_{10}$ with $R_{11}$ or $R_{12}$ forms a three- to seven-membered heterocyclo ring, or $R_{10}$ with $R_{12}$ forms a three- to seven-membered heterocyclo ring.

In the pharmaceutical compositions wherein $R_3$ of formula (I) is hydrogen, it is preferred that $R_6$ is cyano. In an alternative embodiment where $R_3$ is hydrogen, $R_2$ advantageously is selected from heteroaryl including pyridine. Advantageously, when $R_3$ is hydrogen, $R_2$ does not include hydrogen, chlorine, or methyl.

More preferred pharmaceutical compositions are those including a pharmaceutically acceptable diluent or carrier and at least one compound of the formula (I) and/or pharmaceutically acceptable salts thereof, wherein $R_2$ is hydrogen, halogen, lower alkyl, or pyridine;

$R_3$ is hydrogen or —$(CH_2)_zY$;

$R_4$ is hydrogen, methyl, or forms a heterocyclo ring with Y or $R_3$;

$R_5$ is alkyl substituted with aryl, cycloalkyl, or heterocyclo;

$R_6$ is hydrogen, halogen, trifluoromethyl, or cyano;

$R_7$ is hydrogen or trifluoromethyl;

$R_8$ is hydrogen, alkyl, substituted alkyl, or —$(CH_2)_nNR_{13}$, $R_{14}$, wherein $R_{13}$ and $R_{14}$ (i) are independently selected from hydrogen, alkyl, or substituted alkyl, (ii) together form a heterocylco ring;

Y is (i) —$OR_9$, —$CO_2R_9$, —$CH(CO_2R_9)_2$, —$OR_9NR_{10}R_{11}$, —$NR_{10}R_{11}$, —$(C=O)NR_{10}R_{11}$, —$NR_{10}(C=O)R_{12}$ or (ii) together with $R_4$ forms a heterocylo ring;

n is 0, 1, 2, or 3;

z is 0, 1, 2, or 3;

$R_9$ is hydrogen, alkyl, substituted alkyl, alkoxy, heterocyclo, or pentafluorophenyl;

$R_{10}$ and $R_{11}$ are (i) independently selected from hydrogen, alkyl, substituted alkyl, alkoxy, cycloalkyl, substituted cycloalkyl, aryl, heterocyclo, or heteroaryl; or (ii) taken together wherein $R_{10}$ and $R_{11}$ forms a three- to seven-membered heterocyclo ring; and $R_{12}$ is aryl, cycloalkyl, or heteroaryl.

Advantageously, $R_5$ comprises an alkyl substituted with cycloalkyl or an aryl group. When $R_5$ is alkyl substituted with aryl, advantageously the aryl has one to two substituents wherein at least one of the substituents is selected from halogen (e.g., chloro, bromo, fluoro), alkoxy (e.g., methoxy), or a lower alkyl. Advantageously, when $R_9$ comprises a heterocyclo ring with a nitrogen heteroatom, said nitrogen heteroatom has a substituent $X_1$ selected from lower alkyl, substituted alkyl, and cycloalkyl. When $R_4$ and $R_3$ (or Y) form a heterocyclo ring, said ring advantageously is unsubstituted or has at least one substituent $X_2$ comprising $CO_2$ (alkyl).

Most preferred pharmaceutical compositions are those including a pharmaceutically acceptable diluent or carrier and at least one compound of the formula (I) and/or pharmaceutically acceptable salts thereof, wherein $R_2$ is hydrogen or chloro;

$R_3$ is —$(CH_2)_zY$, wherein z is 0, 1, 2, or 3;

$R_4$ is hydrogen;

$R_5$ is 3-chloro-4-methoxyphenylmethyl;

$R_6$ is cyano;

$R_7$ is hydrogen;

$R_8$ is hydrogen, alkyl or substituted alkyl;

Y is —$OR_9$, —$NR_{10}R_{11}$, —$CO_2R_9$, —$(C=O)NR_{10}R_{11}$;

$R_9$ is hydrogen, alkyl, or substituted alkyl; and $R_{10}$ and $R_{11}$ (i) are each independently hydrogen, alkyl, substituted alkyl, aryl, heterocyclo, or heteroaryl; or (ii) together form a five- to seven-membered heterocyclo ring.

Utility

The compounds and compositions of this invention inhibit cGMP PDE, and in particular are potent and selective inhibitors of cGMP PDE 5. Thus, these compounds and compositions are useful in treating cGMP-associated conditions. A "cGMP-associated condition", as used herein, denotes a disorder which can be treated by inhibiting cGMP PDE or elevating the level of cGMP in a subject, wherein treatment comprises prevention, partial alleviation, or cure of the disorder. Inhibition of cGMP PDE or elevation of the cGMP level may occur locally, for example, within certain tissues of the subject, or more extensively throughout the subject being treated for such a disorder. Treatment may be facilitated wherein elevation of the cGMP level potentiates additional beneficial therapeutic effects, such as where elevation of the cGMP level potentiates the effects of endothelium-derived relaxing factor.

The inventive compounds and compositions are useful for treating a variety of cardiovascular diseases including, but not limited to, hypertension, angina (stable, unstable, and variant), (congestive) heart failure, restenosis, atherosclerosis, and dyslipidemia, as well as reduced blood vessel patency, thrombus, both venous and arterial, myocardial infarction, peripheral vascular disease, stroke, bronchitis, chronic asthma, allergic asthma, allergic rhinitis, glaucoma, benign prostate hyperplasia (BPH), and forms of cancer responsive to the inhibition of cGMP PDE. In addition, these compounds are useful in treating sexual dysfunction in both men (erectile dysfunction, for example, due to diabetes mellitus, spinal cord injury, radical prostatectomy, psychogenic etiology or any other cause) and women by improving blood flow to the genitalia, especially, the corpus cavernosum. The compounds and compositions of this invention also are useful in treating diabetes mellitus and related conditions, and diseases of the gastrointestinal tract, such as those characterized by disorders of gut motility, including gastric paresis.

The present invention thus provides methods for treating cGMP-associated conditions, comprising administering to a subject in need thereof an effective amount of at least one compound of the formula I or a salt thereof, and/or pharmaceutical compositions as described above. Other therapeutic agents such as those described below may be employed in combination with the compounds of formula I. In the methods of the present invention, such other therapeutic agent(s) may be administered prior to, simultaneously with, or following the administration of the inventive compound(s) and compositions.

The present invention also provides pharmaceutical compositions capable of treating a cGMP-associated condition, as described above. The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds and compositions of formula I may be administered by any suitable means, for example, orally, such as in the form of tablets, capsules, granules or powders; sublingually; bucally; parenterally, such as by subcutaneous, intravenous, intramuscular or intrasternal injection or infusion techniques (e.g., as sterile injectable aqueous or non-aqueous solutions or suspensions); nasally such as by inhalation spray; topically, such as in the form of a cream or ointment; rectally such as in the form of suppositories; or liposomally; in dosage unit formulations containing non-toxic, pharmaceutically acceptable vehicles or diluents. These compounds may, for example, be administered in a form suitable for immediate release or extended release. Immediate release or extended release may be achieved by the use of suitable pharmaceutical compositions or, particularly in the case of extended release, by the use of devices such as subcutaneous implants or osmotic pumps.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The compounds of formula I may also be delivered through the oral cavity by sublingual and/or buccal administration. Molded tablets, compressed tablets or freeze-dried tablets are exemplary forms that may be used. Exemplary compositions include those formulating the inventive compound(s) with fast-dissolving diluents such as mannitol, lactose, sucrose, and/or cyclodextrins. Also included in such formulations may be high molecular weight excipients such as celluloses (AVICEL®) or polyethylene glycols (PEG). Such formulations may also include an excipient to aid mucosal adhesion such as hydroxypropyl cellulose (HPC), hydroxypropyl methyl cellulose (HPMC), sodium carboxymethyl cellulose (SCMC), maleic anhydride copolymer (e.g., GANTREZ®), and agents to control release such as polyacrylic copolymer (e.g., CARBOPOL 934®). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

Exemplary compositions for topical administration include a topical carrier such as PLASTIBASE® (mineral oil gelled with polyethylene).

The effective amount of a compound of the present invention may be determined by one of ordinary skill in the art, and includes exemplary dosage amounts for an adult human of from about 0.05 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like, subject to cGMP-associated conditions.

The inventive compounds and compositions may be employed alone or in combination with each other and/or other suitable therapeutic agents useful in treating cGMP-associated conditions such as other cGMP PDE inhibitors, particularly other cGMP PDE 5 inhibitors, modulators of the large-conductance calcium-activated potassium (BK) channels, prostanoids, α-adrenergic agonists, endothelin antagonists, angiotensin II (especially, subtype $AT_1$) antagonists, angiotensin converting enzyme (ACE) inhibitors, renin inhibitors, and serotonin ($5\text{-}HT_{2c}$) agonists.

Exemplary of such other therapeutic agents are the following: phentolamine, yohimbine, papaverine, apomorphine, sildenafil, pyrazolopyrimidinones as described in U.S. Pat. Nos. 5,272,147; 5,250,534; 5,426,107; and 5,346,901, quinazolinones as described in U.S. Pat. No. 5,482,941; $AT_1$ antagonists such as from losartan, irbesartan, valsartan, and candesartan; ETA antagonists such as bosentan, ABT-627, and those described in U.S. Pat. No. 5,612,359 and U.S. patent application Ser. No. 60/035,832, filed Jan. 30, 1997; PDE 5 inhibitors selected from imidazoquinazolines (see WO 98/08848), carbazoles (see WO 97/03675, WO 97/03985 and WO 95/19978), imidazopurinones (see WO 97/19947), benzimidazoles (see WO 97/24334), pyrazoloquinolines (see U.S. Pat. No. 5,488,055), quinazolinones as described in U.S. Pat. No. 6,087,368, pyridines as described in U.S. patent application Ser. No. 60/100,655 filed Sep. 16, 1998, anthranilic acid derivatives (see WO 95/18097), fused heterocycles (see WO 98/07430) and thienopyrimidines (see DE 19632423); and $5\text{-}HT_{2c}$ agonists selected from indoles (see *J. Med. Chem.*, 40, 2762–2769 [1997], EP 655440 and EP 657426), and modulators of the large-conductance calcium-activated potassium (BK) channels as described in U.S. Pat. Nos. 5,565,483 and 5,602,169, and in WO 98/04135 and WO98/23273.

The above other therapeutic agents, when employed in combination with the compounds of the present invention, may be used, for example, in those amounts indicated in the Physicians' Desk Reference (PDR) or as otherwise determined by one of ordinary skill in the art.

The following assay can be employed in ascertaining the degree of activity of a compound as a cGMP PDE inhibitor. Compounds described in the following Examples have been tested in this assay, and have shown activity.

PDE Scintillation Proximity Assay Protocol

Sonicated human platelet homogenates are prepared by the method of Seiler, et al. (Seiler, S., Gillespie, E., Arnold, A. J., Brassard, C. L., Meanwell, N. A. and Fleming, J. S., "Imidazoquinoline Derivatives: Potent Inhibitors of Platelet Camp Phosphodiesterase which Elevate Camp Levels and Activate Protein Kinase in Platelets," *Thrombosis Research*, 62: 31–42 (1991)). PDE 5 is abundant in human platelets, and accounts for approximately 90% of the cGMP hydrolytic activity in the homogenates. When necessary, PDE 5 can be resolved from other PDE activities in the homogenates by anion exchange chromatography on a fast protein liquid chromatography system (FPLC) using a Mono-Q anion exchange column (Pharmacia) eluted with a linear gradient of 10 mM–450 mM NaCl.

The phosphodiesterase activity is assayed using a commercially available phosphodiesterase [$^3$H]cGMP scintillation proximity (SPA) assay kit (Amersham). The manufacturer's protocol is followed explicitly except that the reactions are carried out at RT and 3 mM nonradioactive cGMP is included in the suspension of SPA beads to prevent the synthesis of any additional radioactive products.

All documents cited in the present specification are incorporated herein by reference in their entirety.

The following Examples illustrate embodiments of the inventive compounds and starting materials, and are not intended to limit the scope of the claims. For ease of reference, the following abbreviations are used in the Examples, below:

Abbreviations
DMSO=dimethylsulfoxide
HPLC=high pressure liquid chromatography
LRMS=low resolution mass spectrometry
mp=melting point
tlc=thin layer chromatography
RT=room temperature
h=hour(s)
Ac=acetyl
Et=ethyl
Me=methyl
HOAc=acetate
EtOAc=ethyl acetate
EDAC•HCl=ethyl-3-(dimethylamino)propyl carbodiimide, hydrochloride salt
HOBT=hydroxybenztriazole
NMP=N-methyl pyrrolidinone
TEA=triethylamine

PREPARATION OF STARTING MATERIALS

Preparation 1

2-Amino-5-bromo-benzyl alcohol

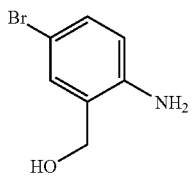

To 13 mmol of methyl 2-amino-5-bromobenzoate in 20 mL of THF at RT was added 65 mmol of 1M lithium tri-tert-butoxyaluminohydride over 10–15 minutes. The solution was heated at reflux for 17 hours. The solution was cooled, poured directly onto silica gel, and eluted with methylene chloride/ethyl acetate; 3:1 followed by 1:1. The product was eluted with 100% methanol to give 2.59 g of the title compound as an off-white solid. MH$^+$: 202; LC: 1.09'.

Preparation 2

Diethyl 2-(4-cyanophenylamino)methylenemalonate

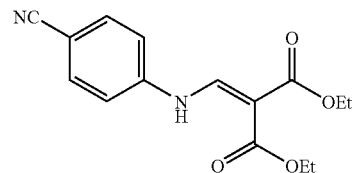

To 5.00 g (42.3 mmol) 4-aminobenzonitrile (Aldrich, 98%) was added 10.1 g (9.41 mL, 46.6 mmol, 1.1 eq) diethylethoxymethylenemalonate (Aldrich, 99%), and the mixture was dissolved in 50 mL toluene (HPLC grade). The solution was refluxed for four hours with a condensor open to the air. The solution was then poured into 200 mL hexane, and the resulting white precipitate was filtered and washed well with more hexane to yield 10.62 g (37.0 mmol, 85% yield) of the title compound as a slightly off-white solid (per LC/MS and $^1$H NMR). LC [MH$^+$] 289, 97% purity.

Preparations 3–6

Diethyl 2-(arylamino)methylenemalonate

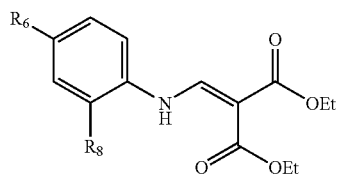

(P1)

Preparations 3–6 of formula (P1) having values for $R_6$, $R_8$ listed in Table 1 were prepared by the same method as in preparation 2, using the corresponding 4 amino-benzene.

TABLE 1

| Preparation | $R_6$ | $R_8$ |
|---|---|---|
| 3 | Et | CN |
| 4 | Cl | CN |
| 5 | HOCH$_2$ | Br |
| 6 | CO$_2$CH$_3$ | Br |

Preparation 7

Diethyl 2-(2-acetoxymethyl-4-bromophenylamino) methylenemalonate

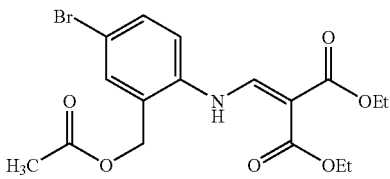

To a solution of 5.83 mmole of product from preparation 5 in 5 ml of pyridine was added 8.74 mmole of acetic anhydride over 15 minutes and the mixture stirred at RT for 1.5 hours. Another 8.74 mmole of acetic anhydride were added, and the mixture stirred at RT for 15.5 hours. Another 2.94 mmole of acetic anhydride were added and the mixture stirred at RT for 4 hours. The mixture was poured into water, and an organic layer extracted with ethyl acetate. The organic layer was washed with water and saturated NaCl, dried over $MgSO_4$, and filtered. The filtrate was concentrated to give 2.10 g of the title compound as an off-white solid. $MH^+$: 416; LC: 4.25'.

Preparation 8

6-Cyano-4-hydroxyquinoline-3-carboxylic acid ethyl ester

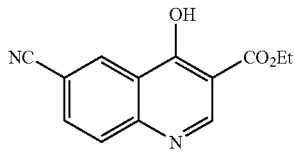

To 100 mL vigorously refluxing diphenyl ether (Aldrich) was added in open air, in portions over the course of one hour, 10.5 g (36.5 mmol) diethyl 2-(4-cyanophenylamino) methylenemalonate. The solution was refluxed for one additional hour. After allowing the solution to cool to below 100° C., it was poured into 200 mL hexane. The resulting precipitate was filtered and washed well with hexane to yield 8.39 g (34.6 mmol, 94%) of the title compound as a light brown solid: $MH^+$: 243, mp>265° C.

Preparations 9–12

6,8-Disubstituted 4-hydroxyquinoline-3-carboxylic acid ethyl esters

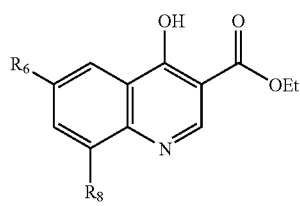

(P2)

Preparations 9–12 of formula (P2) wherein $R_6$ and $R_8$ have the values listed in Table 2, were prepared by the same method as in preparation 8, using an appropriately-substituted diethyl 2-(phenylamino) methylenemalonate.

TABLE 2

| Preparation | $R_6$ | $R_8$ |
|---|---|---|
| 9 | CN | Et |
| 10 | CN | Cl |
| 11 | Br | $AcOCH_2$— |
| 12 | Br | —$CO_2CH_3$ |

Preparation 13

4-Chloro-6-cyanoquinoline-3-carboxylic acid ethyl ester

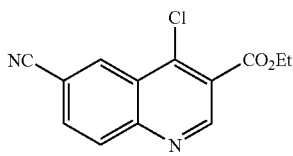

To 9.50 g (39.2 mmol) ethyl 6-cyano-4-hydroxyquinoline-3-carboxylic acid was added 50 mL $POCl_3$ (Aldrich, 99%), and the resulting mixture was refluxed for 48 hrs. The $POCl_3$ was evaporated under reduced pressure, and the residue codistilled once with $CHCl_3$, and twice with toluene. The resulting brown solid was dissolved in $CH_2Cl_2$ and treated with triethylamine until aqueous washings of aliquots had pH>10. The solution was then filtered through a 2" silica pad to yield 10.5 g (40.2 mmol, 103% yield) of the title compound as an off-white crystalline solid; $MH^+$: 261, 97% purity.

Preparations 14–22

4-Chloroquinoline-3-carboxylic acid ethyl esters

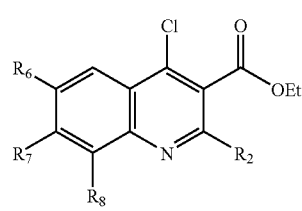

(P3)

The compounds of formula (P3) were prepared, wherein $R_2$, $R_6$, $R_7$, and $R_8$ have the values listed in Table 3, using the same method as in preparation 13, with an appropriately-substituted ethyl 4-hydroxyquinoline-3-carboxylic acid.

TABLE 3

| Preparation | $R_2$ | $R_6$ | $R_7$ | $R_8$ |
|---|---|---|---|---|
| 14 | H | CN | H | Et |
| 15 | H | CN | H | Cl |
| 16 | H | H | $CF_3$ | H |
| 17 | H | $CF_3$ | H | H |
| 18 | H | Br | H | $AcOCH_2$ |
| 19 | H | Br | H | $CO_2CH_3$ |
| 20 | Cl | Br | H | H |
| 21 | Cl | CN | H | H |
| 22 | Cl | CN | H | Et |

Preparations 23 a) and b)

a) Methyl 2-amino-5-cyanobenzoate b) Methyl 2-amino-3-ethyl-5-cyanobenzoate

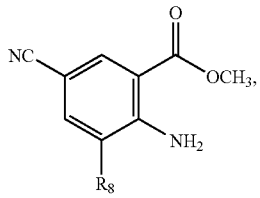

wherein $R_8$ is H or Et

A mixture of methyl 2-amino-5-bromobenzoate (4.6 g, 20 mmol), and CuCN (1.97 g, 22 mmol) in NMP (20 mL) was heated to 190° C. and stirred for 3 h. The reaction mixture was poured into a solution of ethylene diamine (4 mL) in $H_2O$ (16 mL) and extracted with toluene (4×20 mL). The combined extracts were dried ($Na_2SO_4$). Removal of the solvent gave the title compound a) (i.e., $R_8$ is hydrogen). Use of methyl 2-amino-5-bromo-3-ethyl bromobenzoate gave the title compound b) (i.e., $R_8$ is ethyl).

Preparations 24 a) and b)

a) 6-Bromo-2,4-dihydroxylquinoline-3-carboxylic acid ethyl ester b) 6-Cyano-2,4-dihydroxylquinoline-3-carboxylic acid ethyl ester

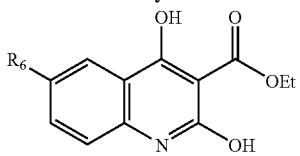

wherein $R_6$ is Br or CN.

Diethyl malonate was added to a freshly prepared solution of sodium ethoxide in ethyl alcohol. The resulting mixture was stirred for 30 min. To it was then added dropwise a solution of 2-amino-5-bromobenzoic acid methyl ester in ethyl alcohol. The resultant mixture was refluxed overnight. The ethyl alcohol was removed under reduced pressure, and the residue was dissolved in water and extracted with EtOAc. The aqueous layer was acidified with glacial AcOH to pH5. The precipitate was collected by filtration to yield 2.6 g, (94% yield) the title compound a) (wherein $R_6$ is Br). Use of 1.76 g (10 mmol) 2-amino-5-cyanobenzoic acid methyl ester yielded 1.7 g (66% yield) of the title compound b) (wherein $R_6$ is CN).

Preparation 25

6-Cyano-2,4-dihydroxyl-8-ethylquinoline-3-carboxylic acid ethyl ester

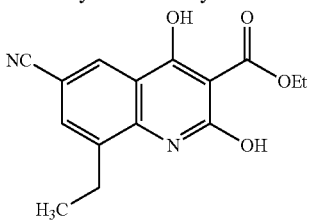

To a solution of methyl 2-amino-5-cyano-3-ethylbenzoate (1.36 g, 6.2 mmol) and TEA (2.6 mL, 18.6 mmol) in THF (50 mL) was added methyl malonyl chloride (1 mL, 9.3 mmol). The mixture was stirred at RT for overnight. Additional TEA (2.6 mL) and methyl malonyl chloride (1 mL) were added, and the reaction was continued for another 24 h. The mixture was diluted with EtOAc and washed with $H_2O$ and brine. The solvent was removed, and the residue was chromatographed (silica gel, EtOAc/hexane, 3:7) to give the amide intermediate. NaH (400 mg, 60% oil dispersion) was washed with dry hexane and dried under nitrogen. To it was added a solution of methyl 2-amino-5-cyano-3-ethylbenzoate (1 g, 3 mmol) in toluene (40 mL), which was followed by dropwise addition of EtOH (4 mL). The resultant mixture was refluxed for overnight. The solvent was removed and the residue was dissolved in $H_2O$ (insoluable particulates were removed by filtration). Upon acidification with HOAc, the title compound (590 mg) was precipitated out and collected by filtration.

Preparation 26

6-Bromo-2-(2-pyridinyl)quinoline-4-carboxylic acid

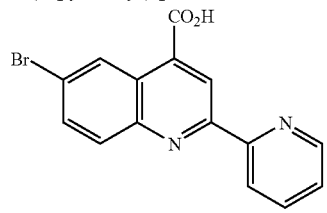

To a suspension of 5-bromo isatin (5 g, 20.5 mmol) and 2-acetylpyridine (2.5 g, 20.5 mmol) in aqueous KOH (1.2 g, 33%) was added EtOH until a solution formed. The mixture was refluxed over night. The reaction mixture was neutralized with HOAc (50%) and filtered. The solid was resuspended in EtOH and filtered to give the title compound (5.5 g). LC: 1.66 and $MH^+$: 329.

Preparation 27

Azido-6-bromo-2-(2-pyridinyl)quinoline-4-carboxylate

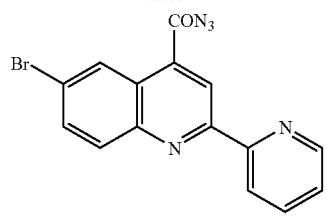

A mixture of 6-bromo-2-(2-pyridine)quinoline-3-carboxylic acid (2.5 g) in $SOCl_2$ (30 mL) was refluxed for 2 h, and the excess $SOCl_2$ was removed. The residue was resuspended in acetone (100 mL). To the suspension was added a solution of $NaN_3$ (0.5 g) in water (50 mL) and stirred for 2 h. The solid product was collected by filtration and washed throughly with water, then dried at 40° C. overnight to give the title compound (2.3 g). LC: 2.13'.

Preparation 28

6-Bromo-4-tbutoxycarbonylamino-2-(2-pyridinyl)quinoline

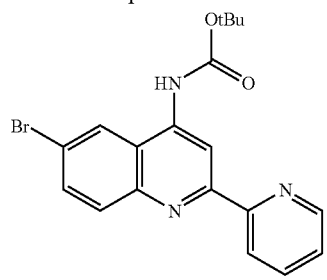

A mixture of preparation 27 (2 g) in toluene (50 mL) was refluxed for 3 h. Then tBuOH (1 mL) was added and continue to reflux for 2 h. The reaction mixture was cooled to RT and filtered. The filtrate was concentrated to give the title compound (2 g).

EXAMPLE 1

4-[[(3-Chloro-4-methoxyphenyl)methyl]amino]-6-cyanoquinoline-3-carboxylic acid ethyl ester

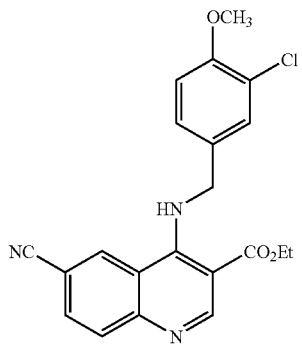

To 10.0 g (38.4 mmol) 4-chloro-6-cyanoquinoline-3-carboxylic acid ethyl ester was added 10.4 g (50 mmol, 1.5 eq) 3-chloro-4-methoxybenzyl amine hydrochloride and 35 mL (228 mmol, 6 eq) diisopropylethylamine (Aldrich, 99.5+%). The mixture was dispersed in 200 mL n-propanol and brought to reflux for two hours. The solution was then poured into 500 mL water. The resulting precipitate was filtered, then washed with 500 mL water, then twice washed with 50 mL absolute ethanol to yield 14.87 g (37.6 mmol, 97% yield) of the title compound as a white fibrous solid after codistilling with absolute ethanol: mp: 161–162° C.; LC/MS (M/Z) 396 [M+H] observed, 97% purity.

EXAMPLES 2–55

4-Aminoquinoline-3-carboxylic acid ethyl esters (Iae)

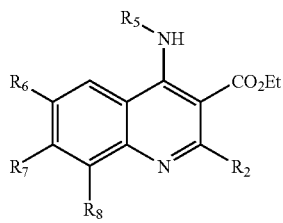

Using the same or similar method of Example 1, compounds having the formula (Iae) were prepared, wherein $R_2$, $R_5$, $R_6$, $R_7$, and $R_8$ have the values listed in Table 4, starting with corresponding 3-carboxylate-4-chloroquinolines and amine hydrochlorides.

TABLE 4

| Ex. No. | —$R_5$ | $R_2$ | $R_6$ | $R_7$ | $R_8$ | HPLC retention time (min.) | MH+ |
|---|---|---|---|---|---|---|---|
| 2 | ![Cl, H3CO, phenyl-ethyl] | H | H | CF$_3$ | H | 3.63 | 439 |
| 3 | ![F-phenyl-ethyl] | Cl | Br | H | H | 4.75 | 437 |
| 4 | ![Cl, H3CO, phenyl-ethyl] | Cl | Br | H | H | 4.56 | 485 |
| 5 | ![Cl, H3CO, phenyl-ethyl] | H | CF$_3$ | H | H | 3.64 | 439 |
| 6 | ![cyclohexyl-CH(CH3)] | H | CN | H | H | 3.73 | 352 |
| 7 | ![cyclohexyl-CH(CH3)] | H | CN | H | H | 3.82 | 352 |

TABLE 4-continued
| Ex. No. | —R$_5$ | R$_2$ | R$_6$ | R$_7$ | R$_8$ | HPLC retention time (min.) | MH$^+$ |
|---|---|---|---|---|---|---|---|
| 8 | 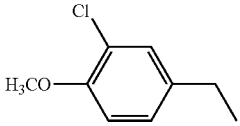 | H | F | H | H | 3.41 | 389 |
| 9 | 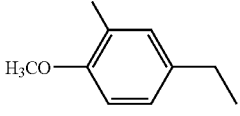 | H | Br | H | CO$_2$nPr | 3.29 | 535 |
| 10 | 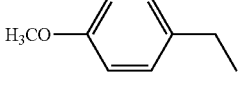 | H | Br | H | CO$_2$Me | 3.52 | 507 |
| 11 | 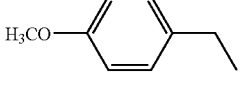 | H | Br | H | H | 2.82 | 449 |
| 12 | 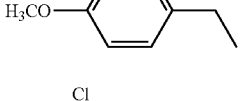 | H | CN | H | Et | 2.78 | 424 |
| 13 | 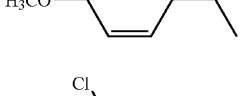 | H | CN | H | Cl | 3.89[b] | 430 |
| 14 | 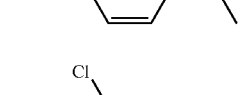 | H | Br | H | AcOCH$_2$ | 1.73[a] | 521 |
| 15 | 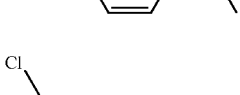 | H | Br | H | Me | 3.68 | 463 |
| 16 | 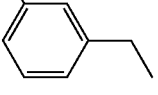 | H | CN | H | Et | 1.56[a] | 394 |
| 17 | 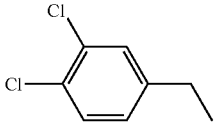 | H | CN | H | Et | 1.68[a] | 428 |

TABLE 4-continued
| Ex. No. | —R$_5$ | R$_2$ | R$_6$ | R$_7$ | R$_8$ | HPLC retention time (min.) | MH$^+$ |
|---|---|---|---|---|---|---|---|
| 18 | 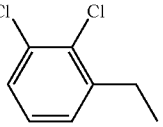 | H | CN | H | Et | 1.65[a] | 428 |
| 19 | 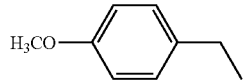 | H | CN | H | Et | 1.46[a] | 390 |
| 20 | 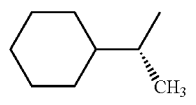 | H | CN | H | Et | 1.73[a] | 380 |
| 21 | 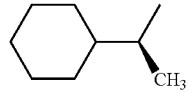 | H | CN | H | Et | 1.73[a] | 380 |
| 22 | 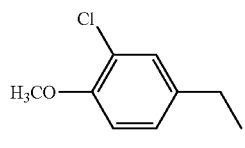 | H | CN | H | CO$_2$nPr | 3.43 | 482 |
| 23 | 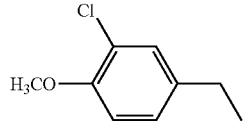 | H | CN | H | CO$_2$Me | 3.11 | 454 |
| 24 | 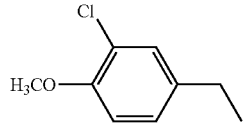 | H | CN | H | CO$_2$Et | 3.27 | 468 |
| 25 | 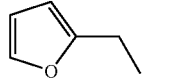 | H | CN | H | Et | 1.23[a] | 350 |
| 26 | 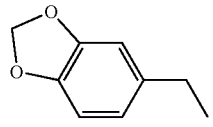 | H | CN | H | Et | 1.33[a] | 404 |
| 27 | 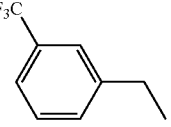 | H | CN | H | Et | 1.49[a] | 428 |
| 28 | 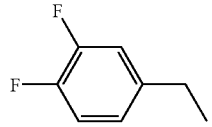 | H | CN | H | Et | 1.38[a] | 396 |
| 29 | 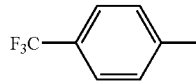 | H | CN | H | Et | 1.49[a] | 428 |

TABLE 4-continued

| Ex. No. | —R$_5$ | R$_2$ | R$_6$ | R$_7$ | R$_8$ | HPLC retention time (min.) | MH$^+$ |
|---|---|---|---|---|---|---|---|
| 30 | 4-(1-methylethyl)phenyl (CH(CH$_3$)$_2$-C$_6$H$_4$-) | H | CN | H | Et | 1.65$^a$ | 402 |
| 31 | 4-tert-butylphenyl (C(CH$_3$)$_3$-C$_6$H$_4$-) | H | CN | H | Et | 1.70$^a$ | 416 |
| 32 | 3,5-dichlorophenyl | H | CN | H | Et | 1.60$^a$ | 428 |
| 33 | 2,5-dimethoxyphenyl | H | CN | H | Et | 1.42$^a$ | 420 |
| 34 | 3,5-dimethoxyphenyl | H | CN | H | Et | 1.39$^a$ | 420 |
| 35 | 4-(trifluoromethoxy)phenyl | H | CN | H | Et | 1.53$^a$ | 444 |
| 36 | 2,6-dichlorophenyl (propyl linker) | H | CN | H | Et | 1.53$^a$ | 442 |
| 37 | 3,4,5-trimethoxyphenyl | H | CN | H | Et | 1.28$^a$ | 550 |
| 38 | 2-fluoro-4-(trifluoromethyl)phenyl | H | CN | H | Et | 1.55$^a$ | 446 |
| 39 | 4-(1,2,3-thiadiazol-5-yl)phenyl | H | CN | H | Et | 1.34$^a$ | 444 |

TABLE 4-continued

| Ex. No. | —R₅ | R₂ | R₆ | R₇ | R₈ | HPLC retention time (min.) | MH⁺ |
|---|---|---|---|---|---|---|---|
| 40 | (S)-1-phenylethyl | H | CN | H | Et | 3.54 | 374 |
| 41 | (R)-1-phenylethyl | H | CN | H | Et | 3.55 | 374 |
| 42 | (S)-1-(4-bromophenyl)ethyl | H | CN | H | Et | 3.94 | 452 |
| 43 | (R)-1-(4-bromophenyl)ethyl | H | CN | H | Et | 3.95 | 452 |
| 44 | (S)-1-(4-methylphenyl)ethyl | H | CN | H | Et | 3.78 | 388 |
| 45 | (R)-1-(4-methylphenyl)ethyl | H | CN | H | Et | 3.77 | 388 |
| 46 | phenylethyl | H | CN | H | Et | 3.26 | 360 |
| 47 | 2-(4-bromophenyl)ethyl | H | CN | H | Et | 3.65 | 438 |
| 48 | 2-(4-methylphenyl)ethyl | H | CN | H | Et | 3.53 | 374 |
| 49 | 2-(4-difluoromethoxyphenyl)ethyl | H | CN | H | Et | 1.38ᵃ | 426 |
| 50 | 2-(4-methylthiophenyl)ethyl | H | CN | H | Et | 1.46ᵃ | 406 |
| 51 | 2-indanylethyl | H | CN | H | Et | 1.46ᵃ | 386 |
| 52 | 3-(3,4-dichlorophenyl)propyl | H | CN | H | Et | 1.80ᵃ | 442 |

TABLE 4-continued

| Ex. No. | —R$_5$ | R$_2$ | R$_6$ | R$_7$ | R$_8$ | HPLC retention time (min.) | MH$^+$ |
|---|---|---|---|---|---|---|---|
| 53 | 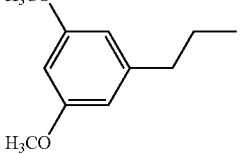 | H | CN | H | Et | 1.41$^a$ | 434 |
| 54 | 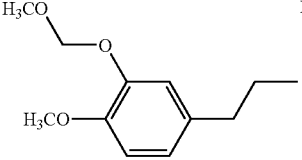 | H | CN | H | Et | 1.36$^a$ | 448 |
| 55 | 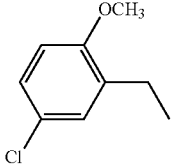 | H | CN | H | Et | 1.52$^a$ | 424 |

EXAMPLE 56

6-Bromo-4-[[(3-Chloro-4-methoxyphenyl)methyl]amino]-8-hydroxymethylquinoline-3-carboxylic acid ethyl ester

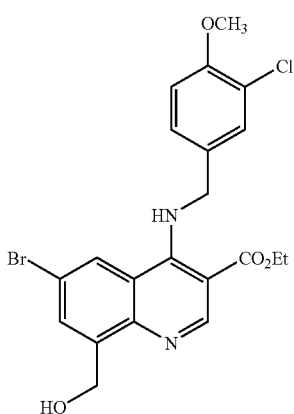

A mixture of 1.84 mmole 6-bromo-4-[[(3-chloro-4-methoxyphenyl)methyl]amino]-8-(acetoxymethyl)quinoline-3-carboxylic acid ethyl ester (i.e., Example 14) and 1.84 mmole of potassium carbonate in 20 mL of ethanol was stirred at RT for 20 hours. The mixture was concentrated, and the residue was diluted with water and extracted with ethyl acetate. The resultant organic layer was dried over MgSO$_4$ and filtered, and the filtrate concentrated to give 0.85 g of the title compound as a tan solid. MS: 481; LC: 3.43'.

EXAMPLE 57

6-Bromo-4-[[(3-Chloro-4-methoxyphenyl)methyl]amino]-8-(chloromethyl)quinoline-3-carboxylic acid ethyl ester

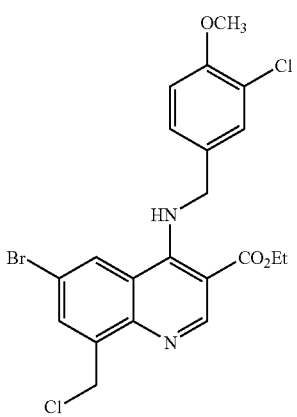

A solution of 1.73 mmole 6-bromo-4-[[(3-chloro-4-methoxyphenyl)methyl)amino)-8-hydroxymethylquinoline-3-carboxylic acid ethyl ester (i.e., Example 56) in 8 ml of thionyl chloride was stirred at RT for 1.5 hours. The solution was concentrated to give 0.86 g of the title compound as an orange foam. MS: 499; LC: 4.15'

EXAMPLE 58

6-Bromo-4-[[(3-Chloro-4-methoxyphenyl)methyl]amino]-8-(N,N-dimethylaminomethyl)quinoline-3-carboxylic acid ethyl ester

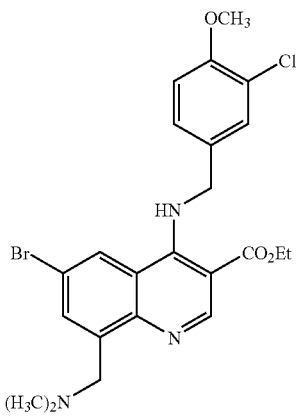

A solution of 0.20 mmole of example 57 and 2 mmole of 2M dimethyamine in 1 ml of THF was stirred at RT for 22 hours. An additional 0.25 ml of 2M dimethylamine in THF was added and the solution stirred for 4 hours. The solution was diluted with ethyl acetate and washed with water. The organic layer was dried over MgSO$_4$ and filtered, and the filtrate was concentrated. The residue was chromatographed on silica gel eluted with methylene chloride followed by methylene chloride/ethyl acetate; 95:5 and finally with ethyl acetate to give 71 mg of the title compound as a beige solid. MS: 507; LC: 3.71'

EXAMPLE 59

4-[[(3-Chloro-4-methoxyphenyl)methyl]amino]-6-cyano-3-quinolinecarboxylic acid

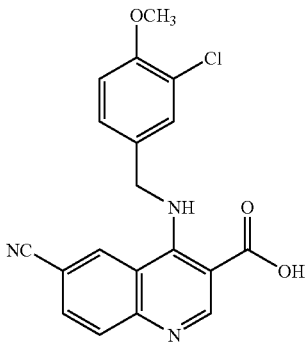

To 8.0 g (20 mmol) 4-(3-Chloro-4-methoxyphenylmethylamino)-6-cyanoquinoline-3-carboxylic acid ethyl ester was added 100 mL THF, 100 mL MeOH and 100 mL 1M NaOH, and the resulting mixture was stirred well. The solids gradually dissolved as the reaction progressed. After 1 h, the THF and most of the MeOH was evaporated under reduced pressure to leave an aqueous slurry of a white solid. The slurry was acidified to pH 1.5 with HCl, stirred well for 1 h, and then filtered and washed well with water to give 7.5 g (20 mmol, ~100% yield) of a white chalky solid. Codistilling twice to dryness with absolute ethanol afforded the title compound: LC/MS: M/Z 368 (M+H) observed, 90+% purity; mp: decomposed 255–260° C. LC 2.93'.

EXAMPLES 60–64

4-[[(3-Choro-4-methoxyphenyl)methyl]amino]-3-quinolinecarboxylic acids

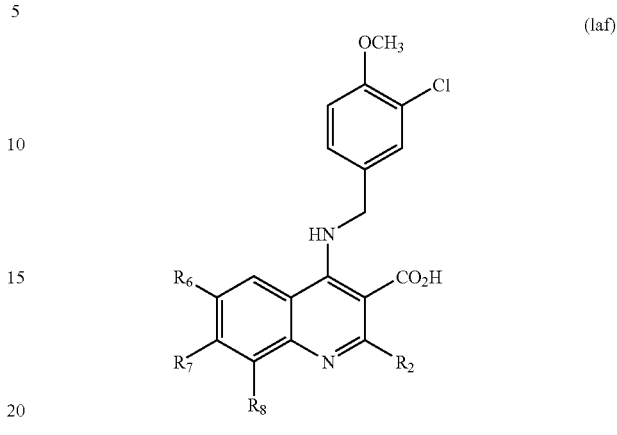

Using the same or similar method as described in Example 59, compounds having the formula (Iaf) were prepared, wherein $R_2$, $R_6$, $R_7$, and $R_8$ have the values listed in Table 5, starting with corresponding 3-carboxylatequinolines.

TABLE 5

| Ex. No. | $R_2$ | $R_6$ | $R_7$ | $R_8$ | HPLC retention time (min.) | MH$^+$ |
|---|---|---|---|---|---|---|
| 60 | H | H | CF$_3$ | H | 3.67 | 411 |
| 61 | Cl | Br | H | H | 4.29 | 455 |
| 62 | H | F | H | H | 3.31 | 361 |
| 63 | H | CN | H | Et | 2.56 | 396 |
| 64 | H | CN | H | Cl | 3.23 | 402 |

EXAMPLE 65

4-[[(3-Chloro-4-methoxyphenyl)methyl]amino]-6-quinolinecarbonitrile

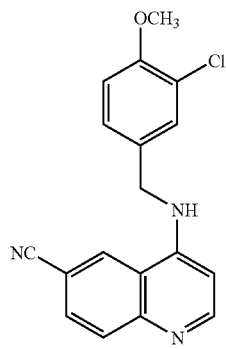

To 2.16 g (5.87 mmol) 4-[[(3-chloro-4-methoxyphenyl)methyl]amino]-6-cyano-3-quinolinecarboxylic acid was added 50 mL diphenyl ether (Aldrich), and nitrogen was vigorously bubbled through this mixture for 20 minutes. The resulting mixture was then heated to 240° C. under nitrogen for 30 minutes. During the course of the reaction, the dispersed starting material slowly dissolved, and gas evolution was observed. The resulting solution was poured into 200 mL hexane, and a precipitated solid was filtered to yield 1.43 g (4.42 mmol, 75% yield) of the title compound as a off-white solid: LC/MS: M/Z 324 (M+H) observed, 96% purity; mp: decomposed 227–230° C. LC: 2.84'.

EXAMPLE 66

4-[[(3-Chloro-4-methoxyphenyl)methyl]amino]-8-ethyl-6-quinolinecarbonitrile

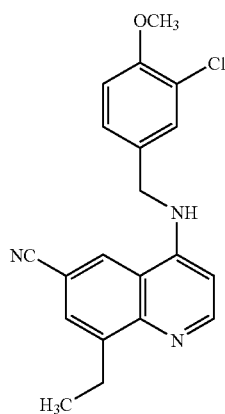

The reaction procedure used was similar to that described for Example 65 with the following changes: 101 mg (0.255 mmol) of 4-[[(3-chloro-4-methoxyphenyl)methyl]amino]-6-cyano-8-ethyl-3-quinolinecarboxylic acid was used to afford 51 mg (57% yield) of the title compound. LC: 1.20' M/Z 352 mp: 206–207° C.

EXAMPLE 67

4-[[(3-Chloro-4-methoxyphenyl)methyl]N-methylamino]-6-quinolinecarbonitrile

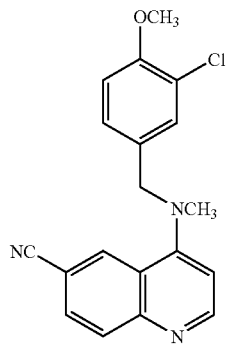

To 250 mg 4-[[(3-chloro-4-methoxyphenyl)methyl]amino]-6-quinolinecarbonitrile (i.e., Example 65) was added 50 mg of NaH, and the mixture was flushed with nitrogen. 5 mL of DMF was added, and it was stirred for half hour. To the mixture was then added 70 μL of CH₃I, and it was stirred at RT. After 1 hour the reaction was quenched with aqueous NH₄Cl and diluted with water, and the precipitate collected by filtration to give (153 mg) of the title compound. LC: 2.48; M/Z 338 m.p. 153–155° C.

EXAMPLE 68

4-[[(3-Chloro-4-methoxyphenyl)methyl]amino]-6-cyanoquinoline-3-carboxylic acid pentafluorophenyl ester

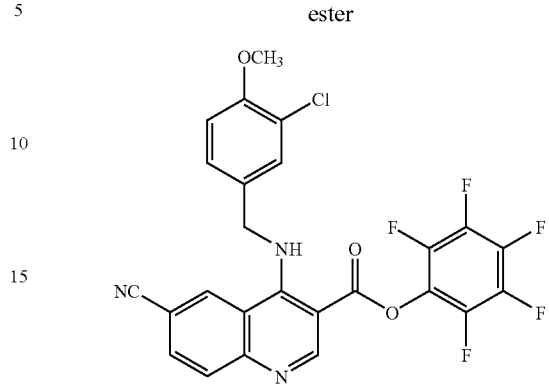

To 275 mg (0.748 mmol) of 4-[[(3-chloro-4-methoxyphenyl)methyl]amino]-6-cyano-3-quinolinecarboxylic acid was added 276 mg (1.50 mmol, 2.0 eq) pentafluorophenol, and the mixture was dispersed in 5 mL anhydrous DMF under nitrogen. To this dispersion was added a solution of 231 mg (1.12 mmol, 1.5 eq) of dicyclohexylcarbodiimide (Aldrich) in 2 mL anhydrous ethyl acetate at RT. The resulting mixture was stirred for 18 hours. The reaction was then diluted with 10 mL EtAc, and the white precipitate was filtered and discarded. The filtrate was concentrated in vacuo, and the residue was triturated with 5% MeOH/95% CH₂Cl₂ to give 164 mg (0.307 mmol, 41% yield) of the title compound as a white solid: LC/MS: M/Z 534 (M+H) observed, 100% purity; mp: decomposed 215–217° C. LC: 4.15.

EXAMPLE 69

4-[[(3-Chloro-4-methoxyphenyl)methyl]amino]-6-cyano-8-ethylquinoline-3-carboxylic acid pentafluorophenyl ester

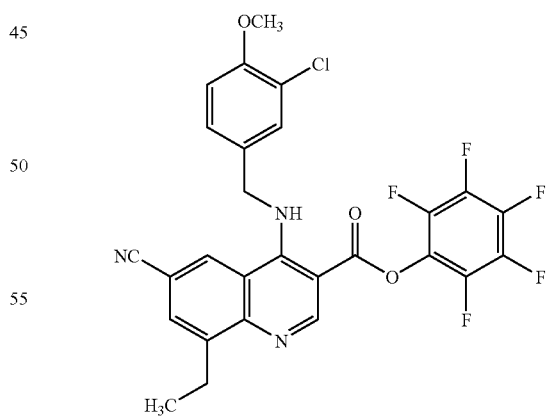

The reaction procedure used was similar to that described for Example 68 with the following changes: 3.95 g (10.0 mmol) 4-[[(3-chloro-4-methoxyphenyl)methyl]amino]-6-cyano-8-ethyl-3-quinolinecarboxylic acid was used to afford 2.81 g (5.00 mmol, 50% yield) of the title compound as a white solid: mp: 169–170° C.; LC: 2.14ᵃ; MH⁺562.

EXAMPLES 70–122

4-[[(3-Chloro-4-methoxyphenyl)methyl]amino]-3-quinolinecarboxamides

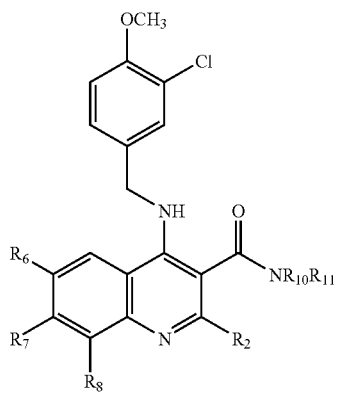

(Iag)

Compounds having the formula (Iag), wherein $R_2$, $R_6$, $R_7$, $R_8$, $R_{10}$, and $R_{11}$ have the values listed in Table 6, were prepared by the following method, starting with corresponding 3-carboxylatequinolines and an appropriate amine:

To 1 eq of 4-[[(3-chloro-4-methoxyphenyl)methyl]amino]-3-quinolinecarboxylic acid pentafluorophenyl ester in THF (approx. 25 mg per 1 mL THF) was added 2 eq of an appropriate primary or secondary amine. The resulting reaction solution was allowed to stir for 18 hours at RT. The THF was then evaporated in vacuo, and the residue was triturated with a 1:1 solution of ether/hexane. The precipitated solid was filtered and washed with 1:1 ether/hexane to yield the desired 4-[[(3-chloro-4-methoxyphenyl)methyl]amino]-3-quinolinecarboxamide. Yields were generally >25%.

TABLE 6

| Ex. No. | $R_2$ | $R_6$ | $R_7$ | $R_8$ | —$NR_{10}R_{11}$ | HPLC retention time (min.) | $MH^+$ |
|---|---|---|---|---|---|---|---|
| 70 | H | H | $CF_3$ | H | —$NH_2$ | 3.35 | 410 |
| 71 | H | H | $CF_3$ | H | HN-CH2-(4-pyridyl) | 3.09 | 501 |
| 72 | H | H | $CF_3$ | H | HN-CH2CH2-(4-pyridyl) | 3.06 | 515 |
| 73 | H | H | $CF_3$ | H | HN-CH2CH2-morpholine | 1.78[a] | 523 |
| 74 | H | H | $CF_3$ | H | HN-(CH2)3-OH | 1.81[a] | 482 |
| 75 | H | H | $CF_3$ | H | HN-cyclohexyl-OH (trans) | 1.92[a] | 508 |
| 76 | H | H | $CF_3$ | H | HN-$CH_3$ | 1.92[a] | 438 |
| 77 | H | H | $CF_3$ | H | 4-hydroxypiperidin-1-yl | 1.73[a] | 494 |
| 78 | H | CN | H | H | HN-CH2-(4-pyridyl) | 2.49 | 458 |

TABLE 6-continued
| Ex. No. | R$_2$ | R$_6$ | R$_7$ | R$_8$ | —NR$_{10}$R$_{11}$ | HPLC retention time (min.) | MH$^+$ |
|---|---|---|---|---|---|---|---|
| 79 | H | CN | H | H | 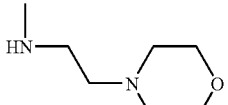 | 2.56 | 480 |
| 80 | H | CN | H | H | 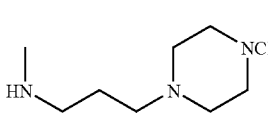 | 2.45 | 507 |
| 81 | H | CN | H | H | 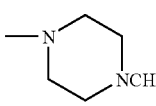 | 2.18 | 450 |
| 82 | H | CN | H | H | —NH$_2$ | 2.73 | 367 |
| 83 | H | CN | H | H | 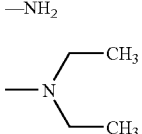 | 2.99 | 423 |
| 84 | H | CN | H | H | 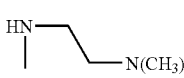 | 1.57[a] | 438 |
| 85 | H | CN | H | H | 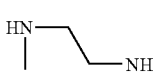 | 2.57 | 410 |
| 86 | H | CN | H | H | 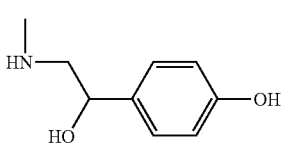 | 1.47[a] | 503 |
| 87 | H | CN | H | H | 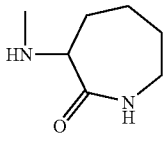 | 1.91[a] | 478 |
| 88 | H | CN | H | H | 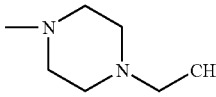 | 1.55 | 464 |
| 89 | H | CN | H | H | 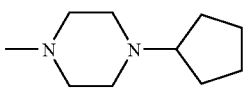 | 1.80 | 504 |
| 90 | H | CN | H | H | 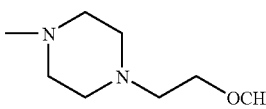 | 1.63 | 494 |
| 91 | H | CN | H | H | 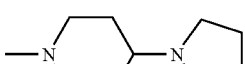 | 1.64 | 504 |
| 92 | H | CN | H | H | 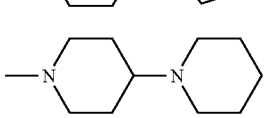 | 1.70 | 518 |

TABLE 6-continued
| Ex. No. | R₂ | R₆ | R₇ | R₈ | —NR₁₀R₁₁ | HPLC retention time (min.) | MH⁺ |
|---|---|---|---|---|---|---|---|
| 93 | H | CN | H | Et | —NH₂ | 2.34 | 395 |
| 94 | H | CN | H | Et | 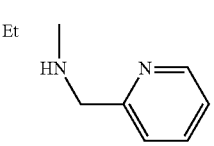 | 2.20 | 486 |
| 95 | H | CN | H | Et | 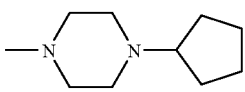 | 2.05 | 532 |
| 96 | H | CN | H | Et | 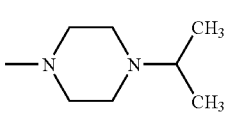 | 1.92 | 506 |
| 97 | H | CN | H | H | 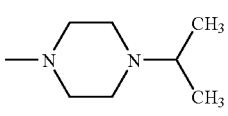 | 2.38 | 478 |
| 98 | Cl | Br | H | H | 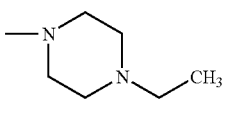 | 3.36 | 551 |
| 99 | Cl | Br | H | H | 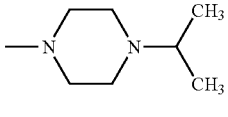 | 3.38 | 565 |
| 100 | Cl | Br | H | H | 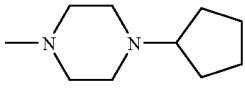 | 3.48 | 591 |
| 101 | Cl | Br | H | H | 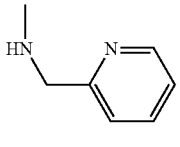 | 3.49 | 545 |
| 102 | Cl | Br | H | H | 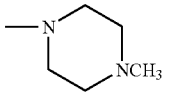 | 2.74 | 537 |
| 103 | Cl | Br | H | H | 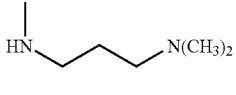 | 1.57ᵃ | 539 |
| 104 | Cl | Br | H | H | 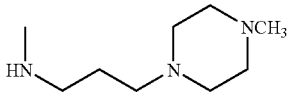 | 1.52ᵃ | 594 |
| 105 | Cl | Br | H | H | 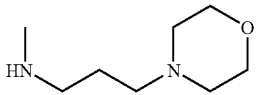 | 1.55ᵃ | 581 |
| 106 | Cl | Br | H | H | 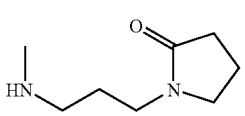 | 3.61 | 579 |

TABLE 6-continued

| Ex. No. | $R_2$ | $R_6$ | $R_7$ | $R_8$ | $-NR_{10}R_{11}$ | HPLC retention time (min.) | $MH^+$ |
|---|---|---|---|---|---|---|---|
| 107 | Cl | CN | H | H | HN-CH2-(2-pyridyl) | 3.09 | 492 |
| 108 | Cl | CN | H | Et | HN-CH2-(2-pyridyl) | 1.73[a] | 520 |
| 109 | H | CN | H | Et | pyrrolidinyl | 1.35[a] | 449 |
| 110 | H | CN | H | Et | 2-(pyrrolidin-1-ylmethyl)pyrrolidin-1-yl | 1.21[a] | 532 |

EXAMPLES 111–179

4-[[(3-Chloro-4-methoxyphenyl)methyl]amino]-6-cyano-3-quinolinecarboxamides

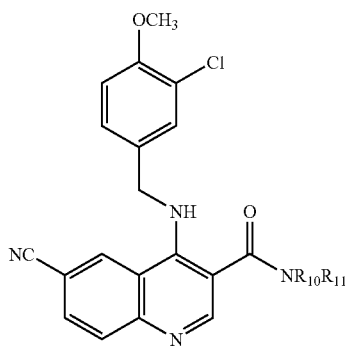

(Iah)

Compounds having the formula (Iah), wherein $R_{10}$ and $R_{11}$ have the values listed in Table 7, were prepared by the following method:

To a solution of 1.0 eq of the appropriate primary amine or 2.0 eq of the appropriate secondary amine in anhydrous THF (3 mL) was added 15 mg 4-[[(3-chloro-4-methoxyphenyl)methyl]amino]-6-cyano-3-quinolinecarboxylic acid pentafluorophenyl ester (0.028 mmol). Where the amine was a hydrohalide salt, 3 eq of triethylamine were also added. The solutions were stirred overnight at 50° C., then filtered and purified by SCX cartridges (2 g capacity, p-toluene sulfonic acid) on a Bohdan SPD robot (10 mL MeOH wash, 10 mL 2M $NH_3$/MeOH elution). The desired 4-[[(3-chloro-4-methoxyphenyl)methyl]amino]-6-cyano-3-quinolinecarboxamide was recovered either by filtration (manual), by concentration of the SCX eluent (by Savant Speedvac), or (if further purification was required) by preparative HPLC (Shimadzu). Average purity: 93% (LC/MS). Average yield: >25%.

TABLE 8

| Ex. No. | $-NR_{10}R_{11}$ | HPLC retention time (min.)[a] | $MH^+$ |
|---|---|---|---|
| 111 | $-N(CH_3)_2$ | 1.63 | 395 |
| 112 | $-N(CH_3)CH_2CH_2CH_3$ | 1.83 | 423 |
| 113 | HN-cyclopentyl | 1.96 | 435 |
| 114 | HN-(CH2)5-CH3 | 2.17 | 451 |
| 115 | HN-CH2CH2-O-CH3 | 1.84 | 439 |
| 116 | HN-CH2CH2-O-CH2CH2-OH | 1.70 | 455 |
| 117 | HN-CH2CH2CH2-O-CH3 | 1.81 | 439 |
| 118 | HN-CH2CH2CH2-O-CH2CH2-CH3 | 2.01 | 467 |

TABLE 8-continued

| Ex. No. | —NR10R11 | HPLC retention time (min.)a | MH+ |
|---|---|---|---|
| 119 | N-CH2-tetrahydrofuran-2-yl | 1.97 | 451 |
| 120 | HN-CH2CH2-OH | 1.69 | 411 |
| 121 | HN-(CH2)3-OH | 1.66 | 425 |
| 122 | HN-(CH2)4-OH | 0.64 | 439 |
| 123 | HN-(CH2)5-OH | 1.77 | 453 |
| 124 | HN-CH(CH2OH)(CH2CH2CH3) | 2.16 | 453 |
| 125 | N(CH2CH2OH)(CH2CH2CH3) | 1.78 | 453 |
| 126 | N(CH2CH2OH)2 | 1.57 | 455 |
| 127 | HN-(trans-4-hydroxycyclohexyl) | 1.70 | 465 |
| 128 | HN-CH2CH2-C(O)OCH3 | 1.78 | 453 |
| 129 | HN-(CH2)3-C(O)CH3 | 1.83 | 467 |
| 130 | HN-CH2CH2-N(C(O)CH3) | 1.66 | 452 |
| 131 | HN-(CH2)3-(2-oxopyrrolidin-1-yl) | 1.77 | 492 |
| 132 | HN-(CH2)3-N(CH2CH3)2 | 1.59 | 466 |
| 133 | N(CH3)(CH2CH2N(CH3)2)(CH2CH3) | 1.49 | 466 |
| 134 | N(CH3)(CH2CH2N(CH2CH3)2)(CH3) | 1.49 | 480 |
| 135 | HN-CH2CH2-N(CH3)(CH2CH2CH2CH3) | 1.74 | 494 |
| 136 | HN-CH2CH2-pyrrolidin-1-yl | 1.60 | 464 |
| 137 | HN-CH2CH2-piperidin-1-yl | 1.66 | 478 |
| 138 | HN-(1-ethylpyrrolidin-3-yl) (diethyl form) | 1.48 | 492 |
| 139 | HN-(CH2)3-NH2 | 1.53 | 424 |
| 140 | HN-CH2-CH(OH)-CH2-NH2 | 1.53 | 440 |
| 141 | HN-CH2-C(CH3)2-CH2-NH2 | 1.58 | 452 |
| 142 | HN-(CH2)3-N(CH3)2 | 1.54 | 452 |
| 143 | HN-(CH2)3-N(CH2CH3)2 | 1.58 | 480 |
| 144 | N(CH3)-(CH2)3-N(CH2CH3)2 | 1.52 | 494 |

TABLE 8-continued

| Ex. No. | —NR₁₀R₁₁ | HPLC retention time (min.)ᵃ | MH⁺ |
|---|---|---|---|
| 145 | (N-methylamino-propyl)-(2-methylpiperidine) | 1.63 | 506 |
| 146 | (N-methylamino-methyl)-(1-ethylpyrrolidine) | 1.59 | 478 |
| 147 | N,N-dimethyl-(1-methylpiperidin-4-yl)amine | 1.46 | 478 |
| 148 | ethyl 4-(methylamino)piperidine-1-carboxylate | 1.96 | 522 |
| 149 | 1-benzyl-4-(methylamino)piperidine | 1.73 | 540 |
| 150 | N-methyl-N'-phenyl-N'-methyl-propane-1,3-diamine | 1.75 | 514 |
| 151 | N-methyl-N',N'-dimethyl-butane-1,4-diamine | 1.54 | 466 |
| 152 | N-methyl-N',N'-dimethyl-hexane-1,6-diamine | 1.63 | 494 |
| 153 | 4-methylmorpholine | 1.63 | 437 |
| 154 | 4-methylthiomorpholine | 1.78 | 453 |
| 155 | 4-(methylamino)morpholine | 1.66 | 452 |
| 156 | 4-(3-(methylamino)propyl)morpholine | 1.55 | 494 |
| 157 | 1-methyl-3-hydroxypyrrolidine | 1.59 | 437 |
| 158 | N-(1-methylpyrrolidin-3-yl)acetamide | 1.59 | 478 |
| 159 | (3R)-N,N-dimethyl-1-methylpyrrolidin-3-amine | 1.43 | 464 |
| 160 | 1-methylpiperidine | 1.83 | 435 |
| 161 | 1-methyl-4-hydroxypiperidine | 1.59 | 451 |
| 162 | 2-(1-methylpiperidin-4-yl)ethanol | 1.69 | 479 |
| 163 | ethyl 1-methylpiperidine-3-carboxylate | 1.91 | 507 |
| 164 | 1-methylpiperidine-4-carboxamide | 1.63 | 478 |
| 165 | 1-methylpiperidine-3-carboxamide | 1.63 | 478 |
| 166 | 8-methyl-1,4-dioxa-8-azaspiro[4.5]decane | 1.90 | 493 |
| 167 | 1-methylpiperazine | 1.43 | 436 |
| 168 | 1-methyl-4-(3-(dimethylamino)propyl)piperazine | 1.43 | 521 |

TABLE 8-continued

| Ex. No. | —NR₁₀R₁₁ | HPLC retention time (min.)ᵃ | MH⁺ |
|---|---|---|---|
| 169 | piperazine-CH₂CH₂OH | 1.41 | 480 |
| 170 | piperazine-cyclohexyl | 1.64 | 518 |
| 171 | piperazine-pyridin-2-yl | 1.48 | 513 |
| 172 | piperazine-pyrimidin-2-yl | 1.76 | 514 |
| 173 | homopiperazine-NH | 1.45 | 450 |
| 174 | homopiperazine-NCH₃ | 1.44 | 464 |
| 175 | HN-CH₂-phenyl | 2.00 | 457 |
| 176 | HN-CH₂-pyridin-3-yl | 1.61 | 458 |
| 177 | HN-CH₂-pyridin-2-yl | 1.87 | 458 |
| 178 | HN-CH₂-C₆H₄-OH | 1.86 | 487 |
| 179 | HN-CH₂-benzodioxole | 2.25 | 501 |

EXAMPLE 180

4-[[(3-Chloro-4-methoxyphenyl)methyl]amino]-3-(hydroxymethyl)-6-quinolinecarbonitrile

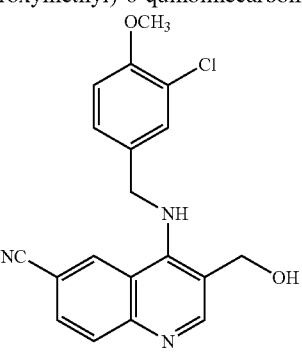

To 530 mg (1.0 mmol) of 4-[[(3-chloro-4-methoxyphenyl)methyl]amino]-6-cyano-3-quinolinecarboxylic acid pentafluorophenyl ester was added 15 mL of anhydrous DMF, and the resulting mixture was cooled to 0° C. A solution of 75 mg of NaBH₄ in 5 mL of anhydrous DMF was added to the reaction mixture, resulting in a clear red solution with gas evolution. After stirring for 1 hour at 0° C., the reaction was quenched with 2% TFA/MeOH, and the solvent was removed under reduced pressure. The oily residue was purified by flash chromatography (silica gel, 3–5% MeOH/CH₂Cl₂) to afford 87 mg (25% yield) of the title compound. LC: 2.60'; MH⁺: 354.

EXAMPLE 181

4-[[(3-Chloro-4-methoxyphenyl)methyl]amino]-8-ethyl-3-(hydroxymethyl)-6-quinolinecarbonitrile

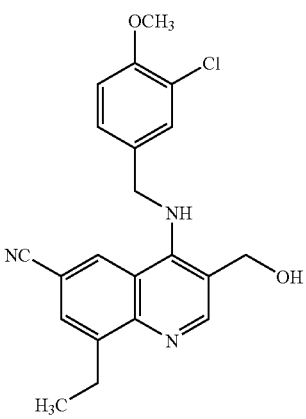

To a suspension of 100 mg (0.236 mmol) of 4-[[(3-chloro-4-methoxyphenyl)methyl]amino]-6-cyano-8-ethylquinoline-3-carboxylic acid ethyl ester in 2.8 mL anhydrous THF under nitrogen, was added 1.2 mL (5.0 eq) of 1M lithium tri-t-butoxyaluminohydride/THF. The resulting mixture was refluxed overnight with stirring. The reaction was quenched with 1 mL of MeOH and partitioned between 75 mL 1M NaOH and 100 mL CH₂Cl₂. The organic phase was washed with 1M NaOH (2×30 mL) and dried over MgSO₄. Removal of the solvent under reduced pressure gave 75 mg (84% yield) of the title compound as a light yellow solid. The analytical sample was obtained by trituration in ether: mp: 188–189° C. LC: 3.15'; MH⁺: 382.

EXAMPLES 182–190

4-Amino-3-(hydroxymethyl)quinolines

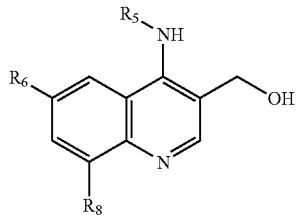

(Iai)

Using the same method of Example 181, compounds having the formula (Iai) were prepared, wherein $R_5$, $R_6$, and $R_8$ have the values listed in Table 8, using an appropriate amine (having the group $R_5$). In Example 190, the reaction was started with 3-ethyl-8-methyldicarboxylatequinoline.

TABLE 8

| Ex. No. | —$R_5$ | $R_6$ | $R_8$ | HPLC retention time (min.) | MH⁺ Found |
|---|---|---|---|---|---|
| 182 | 2-chloro-4-methoxyphenyl-CH(CH₃)- (3-Cl, 4-OCH₃ benzyl with ethyl) | Br | H | 2.41 | 407 |
| 183 | 2-chloro-4-methoxyphenyl-ethyl | CN | Cl | 2.92 | 388 |
| 184 | (R)-1-cyclohexylethyl | CN | Et | 1.50[a] | 338 |
| 185 | (S)-1-cyclohexylethyl | CN | Et | 1.51[a] | 338 |
| 186 | 3,4-dichlorophenyl-ethyl | CN | Et | 1.45[a] | 386 |
| 187 | 2,3-dichlorophenyl-ethyl | CN | Et | 1.43[a] | 386 |
| 188 | 3-chlorophenyl-ethyl | CN | Et | 1.38[a] | 352 |
| 189 | 4-methoxyphenyl-ethyl | CN | Et | 1.25[a] | 348 |
| 190 | 4-methoxyphenyl-ethyl | CN | —(CH₂)OH | 2.59 | 384 |

EXAMPLES 191–194

3-Aminomethyl-4-[[(3-chloro-4-methoxyphenyl)methyl]amino]-6-quinolinecarbonitriles

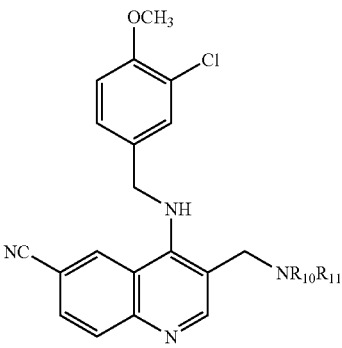

(Iaj)

Compounds having the formula (Iaj) were prepared, wherein $R_{10}$ and $R_{11}$ have the values listed in Table 9, by the following method.

To 70 mg 4-[[(3-chloro-4-methoxyphenyl)methyl]amino]-3-(hydroxymethyl)-6-quinolinecarbonitrile was added 5 mL anhydrous $CH_2Cl_2$ and 70 μL (0.44 mmol, 2.0 eq) diisopropylethylamine, and the resulting solution was cooled to 0° C. under nitrogen. Methanesulfonyl chloride (17 μL, 0.22 mmol, 1.1 eq) was then added, and the resulting reaction solution was stirred at 0° C. for 30 minutes. The solution was then quenched with 0.24 mmol (1.1 eq) of the appropriate amine (having groups $R_{10}$, $R_{11}$), and the resulting solution was stirred for 30 minutes. The solvent was evaporated under reduced pressure and the residue was chromatographed in 5% MeOH/$CH_2Cl_2$ to yield the title compound.

TABLE 9

| Ex. No. | —$NR_{10}R_{12}$ | HPLC retention time (min.) | $MH^+$ |
|---|---|---|---|
| 191 | —N(piperazine)NCH$_3$ | 2.39 | 436 |
| 192 | —$NH_2$ | 1.12 | 353 |
| 193 | HN-CH$_2$-pyridyl | 1.83 | 444 |
| 194 | —N(piperidine) | 1.84 | 421 |

EXAMPLE 195

6-Bromo-4-[[(3-Chloro-4-methoxyphenyl)methyl]amino]-3-[(4-methyl-1-piperazinyl)methyl]quinoline

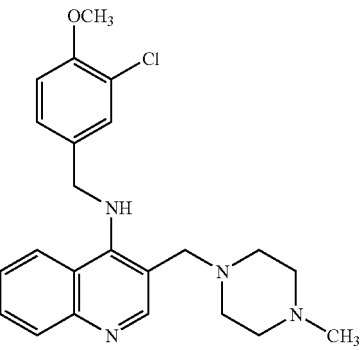

To 4-[[(3-chloro-4-methoxyphenyl)methyl]amino]-3-(hydroxymethyl)-6-bromoquinoline was added $SOCl_2$, and the resulting reaction solution was stirred at RT under nitrogen for 30 minutes. The $SOCl_2$ was then evaporated under reduced pressure, and the residue was left overnight under high vacuum. The yellow residue was redissolved in anhydrous DMF, and this solution was then added to a solution of N-methylpiperazine in anhydrous THF. The resulting reaction solution was stirred for 6 hours at RT, by which time HPLC showed the reaction to be complete. After evaporating the solvent, the crude product was chromatographed in 3% MeOH/$CH_2Cl_2$ to yield the title compound. LC: 2.12'; $MH^+$: 489

EXAMPLES 196–224

3-Aminomethyl-4-[[(3-chloro-4-methoxyphenyl)methyl]amino]-6-quinolinecarbonitriles

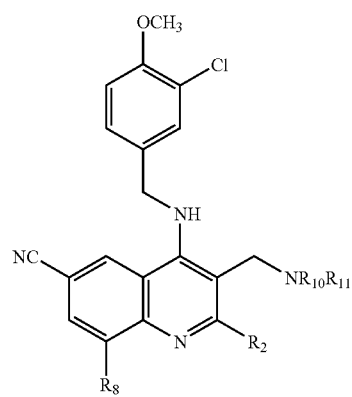

(Iak)

Compounds having the formula (Iak) were prepared, wherein values for $R_2$, $R_8$, $R_{10}$ and $R_{11}$ are as in Table 10, using the same or similar method as in Example 195, starting with the corresponding 4-[[(3-chloro-4-methoxyphenyl)methyl]amino]-3-(hydroxymethyl)-6-quinolinecarbonitrile.

TABLE 10

| Ex. No. | —NR₁₀R₁₁ | R₂ | R₈ | HPLC retention time (mm.) | MH⁺ Found |
|---|---|---|---|---|---|
| 196 | N(CH₃)(propyl)(ethyl) | H | H | 2.55 | 437 |
| 197 | N(CH₃)(isobutyl)(isobutyl) | H | H | 3.43 | 465 |
| 198 | 1-methylpiperidin-3-ol | Cl | H | 1.43ª | 471 |
| 199 | N(CH₃)₂ | H | H | 2.40 | 381 |
| 200 | N(CH₃)(cyclohexyl) | H | H | 2.43 | 449 |
| 201 | (1-methylpyrrolidin-2-yl)methanol | H | H | 1.96 | 437 |
| 202 | 1,3-dimethylpiperidine | H | H | 2.21 | 435 |
| 203 | 2-(methoxymethyl)-1-methylpyrrolidine | H | H | 2.24 | 451 |
| 204 | (1-methylpyrrolidin-2-yl)methanol | H | H | 1.81 | 437 |
| 205 | 1-methylpyrrolidin-3-ol | H | H | 1.60 | 423 |
| 206 | (1-methylpiperidin-4-yl)methanol | H | H | 1.97 | 451 |
| 207 | 1,2-dimethylpiperidine | H | H | 2.33 | 435 |
| 208 | N-methyl-N-cyclopentyl | H | H | 2.61 | 435 |
| 209 | 1-methylpyrrolidin-3-ol | H | H | 1.86 | 423 |
| 210 | 2-ethyl-1-methylpiperidine | H | H | 2.74 | 449 |
| 211 | (1-methylpiperidin-2-yl)methanol | H | H | 2.25 | 451 |
| 212 | 1-methylpiperidin-3-ol | H | H | 1.17ª | 437 |
| 213 | N-(4-chlorobenzyl)amine | H | H | 2.80 | 477 |
| 214 | N-(4-fluorobenzyl)amine | H | H | 2.50 | 461 |
| 215 | N-(4-methoxybenzyl)amine | H | H | 2.45 | 473 |
| 216 | 1-methylpiperidin-3-ol | H | Et | 1.34ª | 465 |
| 217 | N-benzylamine | H | H | 2.40 | 443 |

TABLE 10-continued

| Ex. No. | —NR$_{10}$R$_{11}$ | R$_2$ | R$_8$ | HPLC retention time (mm.) | MH$^+$ Found |
|---|---|---|---|---|---|
| 218 | | H | Et | 1.27$^a$ | 465 |
| 219 | | H | Cl | 1.20$^a$ | 457 |
| 220 | | H | Cl | 1.23$^a$ | 485 |
| 221 | | H | Cl | 1.35$^a$ | 457 |
| 222 | | H | Et | 1.20$^a$ | 451 |
| 223 | | H | Et | 1.45$^a$ | 479 |
| 224 | | H | Et | 1.45$^a$ | 479 |

EXAMPLES 225–263

3-Aminomethyl-4-[[(3-chloro-4-methoxyphenyl)methyl]amino]-6-quinolinecarbonitriles

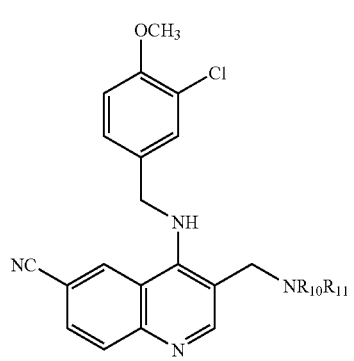

(Ial)

Compounds of formula (Ial) were prepared, wherein R$_{10}$ and R$_{11}$ have the values listed in Table 10, with the following method (Automated parallel synthesis).

A mixture of 1 eq. of 4-[[(3-chloro-4-methoxyphenyl)methyl]amino]-3-chloromethyl-6-cyanoquinoline and 3 eq. of an appropriate amine in THF was reacted for overnight at RT. The reaction mixture was filtered and the filtrate was concentrated. The residue was dissolved in CH$_2$Cl$_2$ and washed with H$_2$O, then dried. Removal of the solvent gives the product.

TABLE 11

| Ex. No. | —NR$_{10}$R$_{11}$ | HPLC retention time (min.) | MH$^+$ |
|---|---|---|---|
| 225 | | 2.54 | 407 |
| 226 | | 2.65 | 421 |
| 227 | | 2.82 | 435 |
| 228 | | 2.99 | 420 |
| 229 | | 2.42 | 411 |
| 230 | | 2.83 | 438 |
| 231 | | 2.4 | 393 |
| 232 | | 2.46 | 407 |
| 233 | | 2.92 | 423 |
| 234 | | 3.18 | 438 |
| 235 | | 2.76 | 435 |
| 236 | | 2.48 | 395 |

TABLE 11-continued

| Ex. No. | —NR₁₀R₁₁ | HPLC retention time (min.) | MH⁺ |
|---|---|---|---|
| 237 | HN-CH(CH₃)-CH₂OH | 2.42 | 411 |
| 238 | HN-CH(CH₃)-CH(CH₃)₂ | 2.99 | 437 |
| 239 | HN-CH(CH₂CH₃)₂ | 2.73 | 423 |
| 240 | HN-CH(CH₃)-CH₂CH₂CH₃ | 2.8 | 423 |
| 241 | HN-CH₂CF₃ | 3.28 | 435 |
| 242 | HN-CH₂C(CH₃)₃ | 2.84 | 423 |
| 243 | HN-CH₃ | 2.44 | 381 |
| 244 | HN-CH₂CH₂OCH₃ | 2.5 | 410 |
| 245 | HN-CH₂CH₂OH | 2.4 | 397 |
| 246 | HN-CH₂CH₂C(CH₃)₃ | 3.07 | 437 |
| 247 | HN-CH₂CH₂CH(CH₃)₂ | 2.91 | 423 |
| 248 | HN-CH₂CH₂CH₃ | 2.55 | 395 |
| 249 | N(CH₃)(CH₂CH₃) | 2.44 | 395 |
| 250 | N(CH₂CH₃)₂ | 2.55 | 409 |
| 251 | N(CH₃)(CH₂CH₂CH₃) | 2.64 | 409 |
| 252 | HN-CH₂CH₂CN | 2.56 | 406 |
| 253 | (CH₃)₂N-CH₂CH(CH₃)₂ | 3 | 423 |
| 254 | HN-CH₂CH₂OCH₂CH₃ | 2.65 | 425 |
| 255 | N(CH₃)₂-CH(CH₃)₂ | 2.54 | 409 |
| 256 | (CH₃)₂N-CH₂CH₂CH(CH₃)₂ | 3.09 | 437 |
| 257 | HN-CH(CH₃)-CH₂OH (S) | 2.44 | 411 |
| 258 | HN-CH(CH₃)-CH₂OH (R) | 2.43 | 410 |
| 259 | HN-CH(CH₃)-CH₂CH₃ (S) | 2.61 | 409 |
| 260 | HN-CH(CH₃)-CH₂CH₃ (R) | 2.61 | 409 |
| 261 | HN-CH₂-(tetrahydrofuran-2-yl) | 2.64 | 437 |
| 262 | N(CH₃)-CH₂CH₂OCH₂CH₃ | 2.71 | 425 |
| 263 | HN-CH₂-(tetrahydrofuran-2-yl) | 2.63 | 437 |

EXAMPLES 264–266

3-(N-acylaminomethyl-4-[[(3-chloro-4-methoxyphenyl)methyl]amino]-6-quinolinecarbonitriles

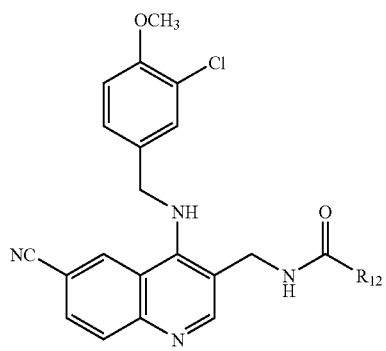

(Iam)

Compounds of formula (Iam) were prepared, wherein $R_{12}$ has the values in Table 12, below. To a mixture of acyl chloride and triethylamine in $CH_2Cl_2$ was added a solution of 3-aminomethyl-4-[[(3-chloro-4-methoxyphenyl)methyl]amino]-6-quinolinecarbonitrile (i.e., Example 192) in dioxane. The reaction mixture was stirred at RT for 1 h. Then the mixture was diluted with EtOAc and washed with water brine and dried ($MaSO_4$). The solvent was removed under reduced pressure and the residue was subjected to flash column chromatography (silica gel, $CH_2Cl_2$/MeOH, 10:1) to give the compounds of Table 12.

TABLE 12

| Ex. No. | $R_{12}$ | HPLC retention time (min.) | MH+ |
|---|---|---|---|
| 264 | phenyl | 2.76 | 457 |
| 265 | cyclohexyl | 3.00 | 463 |

TABLE 12-continued

| Ex. No. | $R_{12}$ | HPLC retention time (min.) | MH+ |
|---|---|---|---|
| 266 | 2-pyridyl | 2.50 | 458 |

EXAMPLES 267–283

3-Alkoxymethyl-4-[[(3-chloro-4-methoxyphenyl)methyl]amino]quinolines

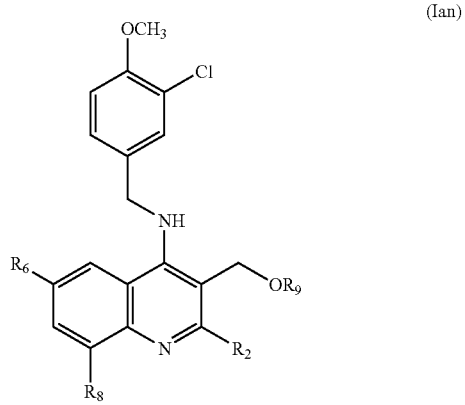

(Ian)

Compounds of formula (Ian) were prepared, wherein $R_2$, $R_6$ $R_8$, and $R_9$ have the values listed in Table 13, with the following method.

To 4-[[(3-chloro-4-methoxyphenyl)methyl]amino]-3-(hydroxymethyl)-6-bromoquinoline was added $SOCl_2$, and the resulting reaction solution was stirred at RT under nitrogen for 30 minutes. The $SOCl_2$ was then evaporated under reduced pressure, and the residue was left overnight under high vacuum. The yellow residue was redissolved in anhydrous DMF, and this solution was then added to a solution of appropriate alcohol in anhydrous THF (or the yellow residue was treated directly with an appropriate liquid alcohol). The resulting reaction solution was stirred for 6 hours at elevated temperature, by which time HPLC showed the reaction to be complete. After evaporating the solvent, the crude product was chromatographed to yield the title compound.

TABLE 13

| Ex. No. | —$R_9$ | $R_2$ | $R_6$ | $R_8$ | HPLC retention time (min.) | MH+ |
|---|---|---|---|---|---|---|
| 267 | propyl-CH3 | H | CN | Et | 1.69a | 424 |
| 268 | —CH3 | H | CN | Et | 3.10 | 396 |
| 269 | ethyl-tetrahydrofuranyl | H | CN | Et | 3.35 | 466 |

TABLE 13-continued

| Ex. No. | —R$_9$ | R$_2$ | R$_6$ | R$_8$ | HPLC retention time (min.) | MH$^+$ |
|---|---|---|---|---|---|---|
| 270 | isobutyl (CH(CH$_3$)CH$_3$ branched) | H | CN | Et | 3.42 | 424 |
| 271 | propyl-CH$_3$ | H | CN | Et | 3.29 | 410 |
| 272 | -CH$_2$CH$_2$CH$_2$-O-CH$_2$CH$_3$ | H | CN | Et | 1.60$^a$ | 454 |
| 273 | -CH$_2$CH$_2$CH$_2$-OH | H | CN | Et | 1.39$^a$ | 426 |
| 274 | (S)-2-ethyl-N-Boc-pyrrolidine | H | CN | Et | 3.91 | 565 |
| 275 | (R)-2-ethyl-N-Boc-pyrrolidine | H | CN | Et | 3.91 | 565 |
| 276 | (R)-3-methyl-N-Boc-pyrrolidine | H | CN | Et | 3.80 | 551 |
| 277 | propyl-CH$_3$ | H | Br | H | 2.78 | 435 |
| 278 | 2-ethyl-N-Boc-pyrrolidine | Cl | CN | H | 2.13$^a$ | 571 |
| 279 | 2-ethyl-N-Boc-pyrrolidine | Cl | CN | Et | 2.37$^a$ | 599 |
| 280 | CH$_3$ | H | Br | ClCH$_2$ | 3.55 | 469 |

TABLE 13-continued

| Ex. No. | —$R_9$ | $R_2$ | $R_6$ | $R_8$ | HPLC retention time (min.) | MH+ |
|---|---|---|---|---|---|---|
| 281 | CH(CH3)2 | H | Br | ClCH2 | 3.78 | 497 |
| 282 | CH2-epoxide | H | CN | Et | 3.18 | 438 |
| 283 | CH3 | H | CN | ClCH2 | 3.17 | 439 |

EXAMPLES 284–288

4-[[(3-Chloro-4-methoxyphenyl)methyl]amino]-8-ethyl-3-[[[(2S)-2-pyrrolidinyl]methoxy]methyl]-6-quinolinecarbonitriles

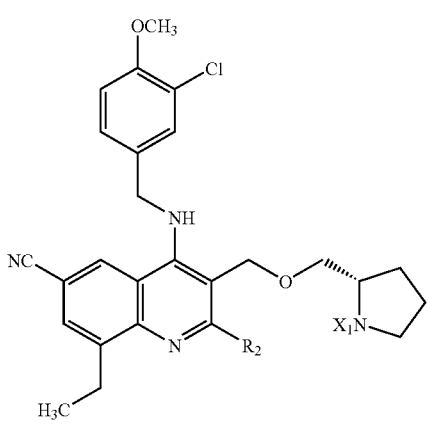

(Iao)

Compounds of formula (Iao) were prepared, wherein $R_2$ and $X_1$ have the values listed in Table 14, with the methods set forth below.

Example 284: Example 275 was treated with TFA/CH2Cl2 (1:1) for 2 hours. The reaction mixture was concentrated. The residue was treated with NaHCO3 (aq. 10%) and extracted with CH2Cl2. The combined extracts were dried (NaSO4) and the solvent was removed. The residue was then purified by preparative HPLC to give Example 284.

Example 285: The same method as Example 285 was used, starting with Example 279.

Example 286: To a solution of Example 284 (30 mg) in THF was added triethylamine (28 μL) which was followed by CH3I (4.5 μL). The resultant mixture was stirred at RT for overnight. The solvent was removed and the residue was chromatographed (silica gel, CH3OH/CHCl3, 1:9) to give Example 286 (5.1 mg).

Examples 287 & 288: To a solution of 0.127 mmole of Example 284 and 1.27 mmole of the ketone in 0.5 mL of methanol cooled in an ice bath was added 0.635 mmole of sodium cyanoborohydride. The ice bath was removed and the suspension stirred for 4 hours to 2 days. The solution was acidified with concentrated HCl and allowed to stir for a few minutes. The solution was neutralized with concentrated NH4OH and extracted with methylene chloride. The organic layer was dried over MgSO4 and filtered, and the filtrate concentrated. The residue was chromatographed on silica gel eluted with methylene chloride/methanol; 95:5 and 9:1 to give Examples 287 and 288.

TABLE 14

| Ex. No. | $R_2$ | $X_1$ | HPLC retention time (min) | MH+ |
|---|---|---|---|---|
| 284 | H | H | 1.27[a] | 465 |
| 285 | Cl | H | 1.83[a] | 499 |
| 286 | H | —CH3 | 1.27[a] | 479 |
| 287 | H | cyclopentyl | 2.72 | 533 |
| 288 | H | —CH(CH3)2 | 2.57 | 507 |

EXAMPLES 289–296

8-Aminomethyl-3-alkoxymethyl-4-[[(3-Chloro-4-methoxyphenyl)methyl]amino]quinolines

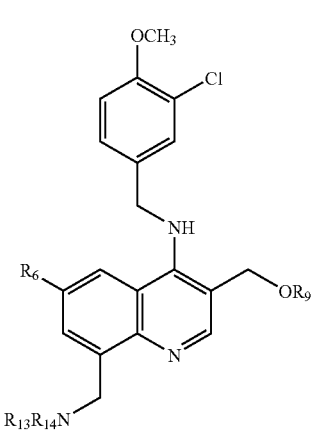

(Iap)

Compounds having the formula (Iap) were prepared, wherein $R_6$, $R_9$, $R_{13}$ and $R_{14}$ have the values listed in Table 15. A solution of 0.072 mmole of 8-chloromethyl quinoline and 0.072 mmole of amine in 0.5 mL of THF was stirred at RT for 16 hours. Another 0.144 mmole of amine were added to the incompleted reactions and the solution stirred for 24 hours. The solution was diluted with water and extracted with ethyl acetate. The organic layer was washed with water, dried over MgSO4, and filtered, and the filtrate was concentrated. The residue was chromatographed on silica gel eluted with methylene chloride/methanol; 98:2, 95:5 followed by methylene chloride/methanol/NH4OH; 90:9:1, to give the products.

TABLE 15

| Ex. # | —R$_9$ | R$_6$ | —NR$_{13}$R$_{14}$ | HPLC retention time (min.) | MH$^+$ |
|---|---|---|---|---|---|
| 289 | —CH(CH$_3$)$_2$ | Br | —N(CH$_3$)$_2$ | 1.54$^a$ | 506 |
| 290 | —CH(CH$_3$)$_2$ | Br | —NHCH$_3$ | 1.47$^a$ | 492 |
| 291 | —CH$_3$ | CN | —N(CH$_3$)$_2$ | 2.81 | 425 |
| 292 | —CH$_3$ | CN | —N-piperazine-NCH$_3$ | 2.15 | 480 |
| 293 | —CH$_3$ | CN | HN-CH$_2$CH$_2$-N(CH$_3$)$_2$ | 1.60 | 468 |
| 294 | —CH$_3$ | CN | H$_3$C-N-piperidine-NCH$_3$ | 2.30 | 508 |
| 295 | —CH$_3$ | CN | HN-CH$_2$CH$_2$-pyrrolidine | 1.62 | 494 |
| 296 | —CH$_3$ | CN | HN-CH$_2$CH$_2$-(2-methylpyrrolidine) | 1.62 | 508 |

EXAMPLES 297–299

3-Alkoxymethyl-4-[[(3-chloro-4-methoxyphenyl)methyl]amino]-8-ethyl-6-quinolinecarbonitriles

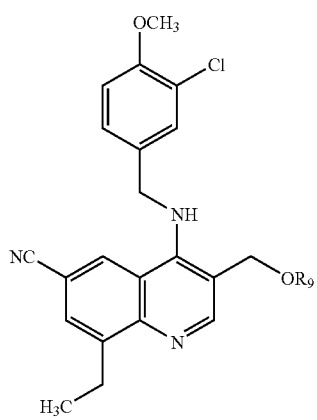

(Iaq)

Compounds having the formula (Iaq) were prepared, wherein R$_9$ is substituted alkyl comprising CH$_2$CH(OH)CH$_2$NR$_{10}$R$_{11}$, and R$_{10}$ and R$_{11}$ have the values listed in Table 16. A solution of 0.11 mmole of Example 282 and 0.22 mmole the appropriate amine in 1 mL of propanol was heated at 60–70° C. for 45 minutes to 30 hours. The solution was concentrated and the residue chromatographed (silica gel, methylene chloride/methanol; 95:5, 9:1 and 4:1) to give the products.

TABLE 16

| Ex. No. | —NR$_{10}$R$_{11}$ | HPLC retention time (min.) | MH$^+$ |
|---|---|---|---|
| 297 | pyrrolidine | 2.51 | 509 |
| 298 | —N(CH(CH$_3$)$_2$)$_2$ | 2.67 | 539 |
| 299 | —N(CH$_3$)$_2$ | 2.48 | 483 |

EXAMPLE 300

3-[[3-[Bis(1-methylethyl)amino]-2-methoxypropoxy]methyl]-4-[[(3-chloro-4-methoxyphenyl)methyl]amino]-8-ethyl-6-quinolinecarbonitrile

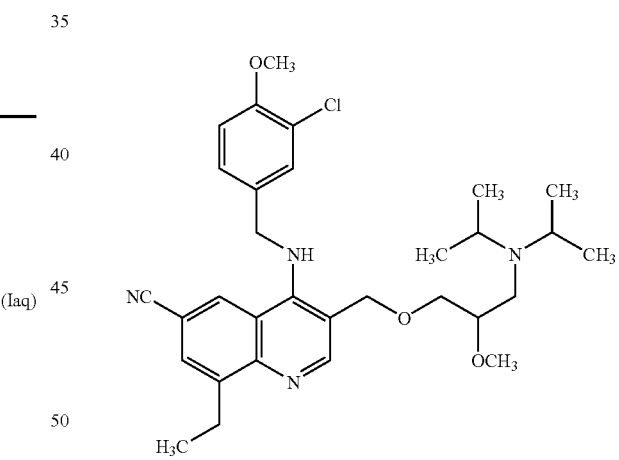

To 0.069 mmole of Example 298 in 0.5 ml of DMF cooled in an ice bath was added 0.072 mmole of 60% NaH in mineral oil. The ice bath was removed, the suspension stirred for 90 minutes, and 0.076 mmole of iodomethane were added. The solution was stirred at RT for 16 hours. An additional 0.038 mmole of 60% NaH in mineral oil and 0.038 mmole of iodomethane were added and the solution stirred for 4 hours. The solution was diluted with water and extracted with ethyl acetate. The organic layer was washed with water and saturated NaCl solution, dried over MgSO$_4$ and filtered, and the filtrate concentrated. The residue was chromatographed on silica gel eluted with methylene chloride/methanol; 95:5 to give 19 mg of the title compound as a colorless oil. MH$^+$: 553; LC: 3.21'.

EXAMPLES 301 and 302

[[4-[[(3-Chloro-4-methoxyphenyl)methyl]amino]-6-cyano-3-quinolinyl]methyl]propanedioic acid dialkyl ester

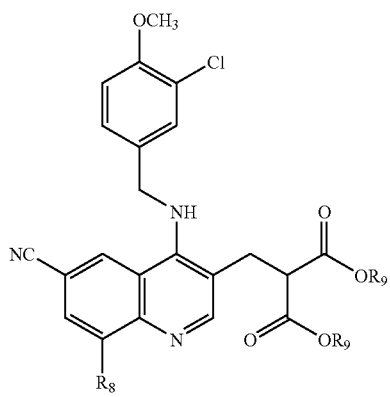
(Iar)

Compounds having the formula (Iar) were prepared, wherein $R_8$ and $R_9$ have the values listed in Table 17. To a dry clean reaction flask was charged 1.3 g (33 mmole) of sodium hydride (60% in mineral oil) and 160 ml of dry THF. To this mixture was added dropwise 6.5 g (30 mmole) of di-t-butylmalonate over a period of 20 minutes at RT. After completion of the addition, the reaction mixture was stirred at RT for an additional 15 minutes then cooled to –78° C. A solution of the 3-chloromethyl quinoline (~10 mmole) in 160 ml of DMF was added via an addition funnel over a period of 1 hour. After completion of the addition, the reaction mixture was stirred at –78° C. for one more hour then was quenched with water at 0° C. THF was removed under reduced pressure. The resulting solution was diluted with ethyl ether washed with water three times, brine, dried over sodium sulfate, and concentrated, and then purified by column chromatograph (silica gel $CH_2Cl_2$/MeOH, 100:5) to give the product (2.75 g).

TABLE 17

| Ex. No. | $R_8$ | $R_9$ | HPLC retention time (min.) | MH+ |
|---|---|---|---|---|
| 301 | H | t-butyl | 3.19 | 552 |
| 302 | Et | Me | 3.22 | 496 |

EXAMPLE 303

4-[[(3-Chloro-4-methoxyphenyl)methyl]amino]-6-cyano-3-quinolinepropanoic acid

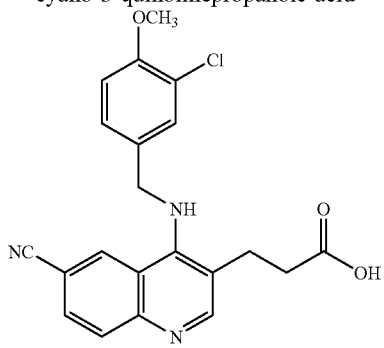

Example 301 (200 mg) was dissolved in 10 ml of ethanol. 1 ml of 10% LiOH/$H_2O$ aqueous solution was added. The reaction solution was stirred at 45° C. for 2 hours. Ethanol was removed under reduced pressure. The resulting aqueous solution was adjusted to pH=4 with 10% HCl. The solid was collected by filtration, rinsed with water, dried to afford 160 mg slightly yellow solid. This product (300 mg) was mixed in 0.3 ml of DMF and stirred at 130° C. for 10 minutes. The reaction mixture was cooled to room temperature. Water was added. The solid was collected by filtration, rinsed with water, and dried to afford 244 mg of the title compound. LC: 2.20', MH+: 396

EXAMPLES 304–306

1-[(3-Chloro-4-methoxyphenyl)methyl]-1,2,3,4-tetrahydro-2-oxobenzo[h]-1,6-naphthyridine-9-carbonitriles

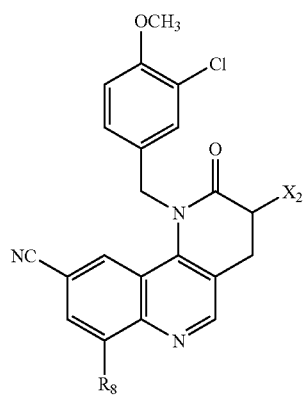
(Ias)

Compounds having the formula (Ias) wherein $R_8$ and $X_2$ have the values listed in Table 18, were prepared as follows.

Examples 304–305: To a suspension of NaH (123 mg) in THF (10 mL) was added dimethylmalonate (370 mg) dropwise. The mixture was stirred at RT for 15 min. then cooled to –78° C. A solution of 4-(3-chloro-4-methoxyphenylmethylamino)-3-chloromethyl-6-cyanoquinoline (0.85 mmol) in DMF was then added dropwise. The reaction was quenched at low temperature and diluted with $Et_2O$ then washed with water. The ether layer was concentrated and the residue was purified by flash column (silica gel, $CH_2Cl_2$/MeOH, 100:4) to give example 303 (160 mg).

Example 306: A mixture of the compound of Example 305 (20 mg), 1-isopropylpypirizine (13 mg), EDAC·HCl (20 mg), HOBT·$H_2O$ (15 mg) and DMAP (trace) in pyridine (1.5 mL) was stirred at RT for over night. The crude product was purified by preparative HPLC to give Example 306.

TABLE 18

| Ex. No. | $R_8$ | —$X_2$ | HPLC retention time (min.) | MH+ |
|---|---|---|---|---|
| 304 | H | —(C=O)$OCH_3$ | 2.91 | 436 |
| 305 | Et | —(C=O)$OCH_3$ | 4.04 | 464 |
| 306 | H | H | 2.79 | 378 |

EXAMPLES 307–314

4-[[(3-Chloro-4-methoxyphenyl)methyl]amino]-6-cyano-N-alkyl-3-quinolinepropanamides

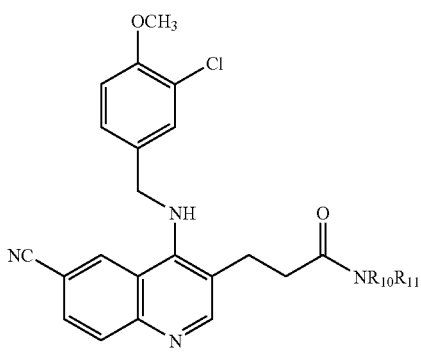

(Iat)

Compounds of formula (Iat) wherein $R_{10}$ and $R_{11}$ have the values listed in Table 19, were prepared as follows.

The compound of Example 303 (20 mg, 0.05 mmole) was mixed with BOP reagent (44 mg, 0.1 mmole) in 3 ml of pyridine and stirred at RT for 3 hours. The resulting reaction mixture was purified by preparative HPLC to afford a cream-colored solid.

TABLE 19

| Ex. No. | —NR$_{10}$R$_{11}$ | HPLC retention time (min.) | MH$^+$ |
|---|---|---|---|
| 307 | | 2.16 | 486 |
| 308 | NH$_3$ | 2.08 | 395 |
| 309 | | 2.22 | 478 |
| 310 | | 2.34 | 423 |
| 311 | | 2.14 | 506 |
| 312 | | 2.66 | 463 |
| 313 | | 2.91 | 477 |
| 314 | | 2.71 | 463 |

EXAMPLE 315

6-Bromo-N-[(3-chloro-4-methoxyphenyl)methyl]-2-(2-pyridinyl)-4-quinolinamine

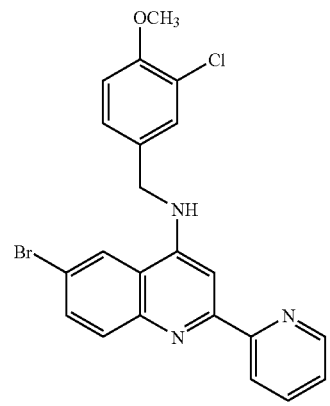

To a suspension of 6-bromo-2-(2-pyridine)quinoline-3-aminotbutyl ester (preparation 28) (300 mg) in DMF (10 mL) was added a solution of HMDSNa in THF (1 M, 0.9 mL) at RT to generate a brown solution. Then 3-chloro-4-methoxybenzyl chloride (160 mg) was added. The reaction mixture was stirred at RT for 2 h. An additional solution of HMDSNa in THF (0.9 mL) and 3-chloro-4-methoxybenzyl chloride (2 eq) was added and continue to stir. When the starting material was consumed, the reaction mixture was treated with TFA. Removal of the solvent and the residue was redissolved in EtOAc and washed with 1 N NaOH and water. Removal of the solvent and tritrated with Et$_2$O to give the title compound (163 mg) as a light yellow solid. LC: 1.73' MH$^+$: 454

The invention claimed is:

1. A compound having the formula:

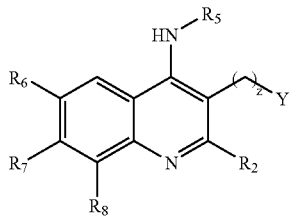

or a pharmaceutically-acceptable salt thereof, wherein:

$R_5$ is
 (i) alkyl or substituted alkyl;
$R_2$ is hydrogen, halogen, $C_{1-4}$alkyl, or $C_{1-4}$haloalkyl;
Y is selected from —NR$_{10}$R$_{11}$, —(C=O)NR$_{10}$R$_{11}$, and —NR$_{10}$(C=O)R$_{12}$;
$R_6$ and $R_7$ are selected from hydrogen, halogen, $C_{1-4}$alkyl, trifluoromethyl, alkoxy, nitro, and cyano;
$R_8$ is hydrogen, alkyl, substituted alkyl, or CO$_2$alkyl;
$R_{10}$, $R_{11}$, and $R_{12}$ are (i) independently selected from heterocyclo and heteroaryl; or (ii) taken together, wherein $R_{10}$ forms a three- to seven-membered heterocyclo ring with $R_{11}$ or $R_{12}$ or $R_{11}$ forms a three- to seven-membered heterocyclo ring with $R_{12}$; and
z is 0, 1, 2, or 3.

2. A compound according to claim 1, or a pharmaceutically-acceptable salt thereof, wherein:
R$_5$ is

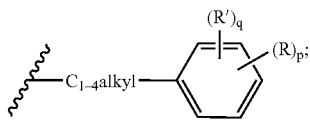

wherein
R and R' are independently selected from halogen, C$_{1-4}$alkyl, CF$_3$, OCF$_3$, OCHF$_2$, O(C$_{1-4}$alkyl) or S(C$_{1-4}$alkyl); and
p is 0 or 1, and q is 0, 1 or 2, provided that p and q together teat least one.

3. A compound according to claim 2, or a pharmaceutically-acceptable salt thereof, in which:
R is —OC$_{1-4}$alkyl;
R' is halogen;
R$_2$ is hydrogen or halogen;
R$_6$ is cyano;
R$_7$ is hydrogen; and
R$_8$ is hydrogen, alkyl, or substituted alkyl.

4. A compound according to claim 1, or a pharmaceutically-acceptable salt thereof, wherein R$_2$ and R$_7$ are hydrogen.

5. A compound according to claim 1, or a pharmaceutically-acceptable salt thereof, wherein R$_5$ is

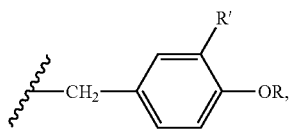

wherein R' is halogen and R is C$_{1-4}$alkyl.

6. A compound according to claim 1, or a pharmaceutically-acceptable salt thereof, wherein R$_6$ is cyano.

7. A compound according to claim 1, or a pharmaceutically-acceptable salt thereof, wherein R$_8$ is hydrogen or C$_{1-4}$alkyl.

8. A compound according to claim 1, selected from:
(i) 4-[[(3-Chloro-4-methoxypheny)methyl]amino]-7-(trifluoromethyl)-3-quinolinecarboxamide;
4-[[(3-Chloro-4-methoxypheny)methyl]amino]-N-(4-pyridinylmethyl)-7-(trifluoromethyl)-3-quinolinecarboxamide;
4-[[(3-Chloro-4-methoxypheny)methyl]amino]-N-[2-(4-pyridinyl)ethyl]-7-(trifluoromethyl)-3-quinolinecarboxamide;
4-[[(3-Chloro-4-methoxyphenyl)methyl]amino]-N-[2-(4-morpholinyl)ethyl]-7-(trifluoromethyl)-3-quinolinecarboxamide;
4-[[(3-Chloro-4-methoxyphenyl)methyl]amino]-N-(4-hydroxybutyl)-7-(trifluoromethyl)-3-quinolinecarboxamide;
trans-4-[[(3-Chloro-4-methoxyphenyl)methyl]amino]-N-(4-hydroxycyclohexyl)-7-(trifluoromethyl)-3-quinolinecarboxamide;
4-[[(3-Chloro-4-methoxyphenyl)methyl]amino]-N-ethyl-7-(trifluoromethyl)-3-quinolinecarboxamide;
4-[[(3-Chloro-4-methoxyphenyl)methyl]amino]-6-cyano-N-(4-pyridinylmethyl)-3-quinolinecarboxamide;
4-[[(3-Chloro-4-methoxyphenyl)methyl]amino]-6-cyano-N-[2-(4-morpholinyl)ethyl]-3-quinolinecarboxamide;
4-[[(3-Chloro-4-methoxyphenyl)methyl]amino]-6-cyano-N-[3-(4-methyl-1-piperazinyl)propyl]-3-quinolinecarboxamide;
4-[[(3-Chloro-4-methoxyphenyl)methyl]amino]-6-cyano-3-quinolinecarboxamide;
4-[[(3-Chloro-4-methoxyphenyl)methyl]amino]-6-cyano-N,N-diethyl-3-quinolinecarboxamide;
4-[[(3-Chloro-4-methoxyphenyl)methyl]amino]-6-cyano-N-[2-(dimethylamino)ethyl]-3-quinolinecarboxamide;
N-(2-Aminoethyl)-4-[[(3-chloro-4-methoxyphenyl)methyl]amino]-6-cyano-3-quinolinecarboxamide;
4-[[(3-Chloro-4-methoxyphenyl)methyl]amino]-6-cyano-N-[2-hydroxy-2-(4-hydroxyphenyl)ethyl]-3-quinolinecarboxamide;
4-[[(3-Chloro-4-methoxyphenyl)methyl]amino]-6-cyano-8-ethyl-3-quinolinecarboxamide;
4-[[(3-Chloro-4-methoxyphenyl)methyl]amino]-6-cyano-8-ethyl-N-(2-pyridinylmethyl)-3-quinolinecarboxamide;
6-Bromo-2-chloro-4-[[(3-chloro-4-methoxyphenyl)methyl]amino]-N-(2-pyridinylmethyl)-3-quinolinecarboxamide;
6-Bromo-2-chloro-4-[[(3-chloro-4-methoxyphenyl)methyl]amino]-N-[3-(dimethylamino)propyl]-3-quinolinecarboxamide;
6-Bromo-2-chloro-4-[[(3-chloro-4-methoxyphenyl)methyl]amino]-N-[3-(4-methyl-1-piperazinyl)propyl]-3-quinolinecarboxamide;
6-Bromo-2-chloro-4-[[(3-chloro-4-methoxyphenyl)methyl]amino]-N-[3-(4-morpholinyl)propyl]-3-quinolinecarboxamide;
6-Bromo-2-chloro-4-[[(3-chloro-4-methoxyphenyl)methyl]amino]-N-[3-(2-oxo-1-pyrrolidinyl)propyl]-3-quinolinecarboxamide;
2-chloro-4-[[(3-chloro-4-methoxyphenyl)methyl]amino]-6-cyano-N-(2-pyridinylmethyl)-3-quinolinecarboxamide;
2-chloro-4-[[(3-chloro-4-methoxyphenyl)methyl]amino]-6-cyano-8-ethyl-N-(2-pyridinylmethyl)-3-quinolinecarboxamide;
4-[[(3-Chloro-4-methoxyphenyl)methyl]amino]-6-cyano-N,N-dimethyl-3-quinolinecarboxamide;
4-[[(3-Chloro-4-methoxyphenyl)methyl]amino]-6-cyano-N-methyl-N-propyl-3-quinolinecarboxamide;
4-[[(3-Chloro-4-methoxyphenyl)methyl]amino]-6-cyano-N-cyclopentyl-3-quinolinecarboxamide;
4-[[(3-Chloro-4-methoxyphenyl)methyl]amino]-6-cyano-N-hexyl-3-quinolinecarboxamide;
4-[[(3-Chloro-4-methoxyphenyl)methyl]amino]-6-cyano-N-(2-ethoxyethyl)-3-quinolinecarboxamide;
4-[[(3-Chloro-4-methoxyphenyl)methyl]amino]-6-cyano-N-[2-(2-hydroxyethoxy)ethyl]-3-quinolinecarboxamide;
4-[[(3-Chloro-4-methoxyphenyl)methyl]amino]-6-cyano-N-(3-methoxypropyl)-3-quinolinecarboxamide;
4-[[(3-Chloro-4-methoxyphenyl)methyl]amino]-6-cyano-N-(3-propoxypropyl)-3-quinolinecarboxamide;
4-[[(3-Chloro-4-methoxyphenyl)methyl]amino]-6-cyano-N-[(tetrahydro-2-furanyl)methyl]-3-quinolinecarboxamide;
4-[[(3-Chloro-4-methoxyphenyl)methyl]amino]-6-cyano-N-(2-hydroxyethyl)-3-quinolinecarboxamide;
4-[[(3-Chloro-4-methoxyphenyl)methyl]amino]-6-cyano-N-(3-hydroxypropyl)-3-quinolinecarboxamide;

4-[[(3-Chloro-4-methoxyphenyl)methyl]amino]-6-cyano-N-(4-hydroxybutyl)-3-quinolinecarboxamide;
4-[[(3-Chloro-4-methoxyphenyl)methyl]amino]-6-cyano-N-(5-hydroxypentyl)-3-quinolinecarboxamide;
4-[[(3-Chloro-4-methoxyphenyl)methyl]amino]-6-cyano-N-[1-(hydroxymethyl)butyl]-3-quinolinecarboxamide;
4-[[(3-Chloro-4-methoxyphenyl)methyl]amino]-6-cyano-N-(2-hydroxyethyl)-N-propyl-3-quinolinecarboxamide;
4-[[(3-Chloro-4-methoxyphenyl)methyl]amino]-6-cyano-N,N-bis(2-hydroxyethyl)-3-quinolinecarboxamide;
trans-4-[[(3-Chloro-4-methoxyphenyl)methyl]amino]-6-cyano-N-(4-hydroxycyclohexyl)-3-quinolinecarboxamide;
3-[[[4-[[(3-Chloro-4-methoxyphenyl)methyl]amino]-6-cyano-3-quinolinyl]carbonyl]amino]propanoic acid methyl ester;
4-[[[4-[[(3-Chloro-4-methoxyphenyl)methyl]amino]-6-cyano-3-quinolinyl]carbonyl]amino]butanoic acid methyl ester;
N-[2-(Acetylamino)ethyl]-4-[[(3-chloro-4-methoxyphenyl)methyl]amino]-6-cyano-3-quinolinecarboxamide;
4-[[(3-Chloro-4-methoxyphenyl)methyl]amino]-6-cyano-N-[3-(2-oxo-1-pyrrolidinyl)propyl]-3-quinolinecarboxamide;
4-[[(3-Chloro-4-methoxyphenyl)methyl]amino]-6-cyano-N-[2-(diethylamino)ethyl]-3-quinolinecarboxamide;
4-[[(3-Chloro-4-methoxyphenyl)methyl]amino]-6-cyano-N-[2-(dimethylamino)ethyl]-N-ethyl-3-quinolinecarboxamide;
4-[[(3-Chloro-4-methoxyphenyl)methyl]amino]-6-cyano-N-[2-(diethylamino)ethyl]-N-methyl-3-quinolinecarboxamide;
N-[2-(Butylethylamino)ethyl]-4-[[(3-chloro-4-methoxyphenyl)methyl]amino]-6-cyano-3-quinolinecarboxamide;
4-[[(3-Chloro-4-methoxyphenyl)methyl]amino]-6-cyano-N-[2-(1-pyrrolidinyl)ethyl]-3-quinolinecarboxamide;
4-[[(3-Chloro-4-methoxyphenyl)methyl]amino]-6-cyano-N-[2-(1-piperidinyl)ethyl]-3-quinolinecarboxamide;
N-(3-Aminopropyl)-4-[[(3-chloro-4-methoxyphenyl)methyl]amino]-6-cyano-3-quinolinecarboxamide;
N-(3-Amino-2-hydroxypropyl)-4-[[(3-chloro-4-methoxyphenyl)methyl]amino]-6-cyano-3-quinolinecarboxamide;
N-(3-Amino-2,2-dimethylpropyl)-4-[[(3-chloro-4-methoxyphenyl)methyl]amino]-6-cyano-3-quinolinecarboxamide;
4-[[(3-Chloro-4-methoxyphenyl)methyl]amino]-6-cyano-N-[3-(dimethylamino)propyl]-3-quinolinecarboxamide;
4-[[(3-Chloro-4-methoxyphenyl)methyl]amino]-6-cyano-N-[3-(diethylamino)propyl]-3-quinolinecarboxamide;
4-[[(3-Chloro-4-methoxyphenyl)methyl]amino]-6-cyano-N-[3-(diethylamino)propyl]-N-methyl-3-quinolinecarboxamide;
4-[[(3-Chloro-4-methoxyphenyl)methyl]amino]-6-cyano-N-[3-(2-methyl-1-piperidinyl)propyl]-3-quinolinecarboxamide;
4-[[(3-Chloro-4-methoxyphenyl)methyl]amino]-6-cyano-N-[(1-ethyl-2-pyrrolidinyl)methyl]-3-quinolinecarboxamide;
4-[[(3-Chloro-4-methoxyphenyl)methyl]amino]-6-cyano-N-[3-(methylphenylamino)propyl]-3-quinolinecarboxamide;
4-[[(3-Chloro-4-methoxyphenyl)methyl]amino]-6-cyano-N-[4-(dimethylamino)butyl]-3-quinolinecarboxamide;
4-[[(3-Chloro-4-methoxyphenyl)methyl]amino]-6-cyano-N-[6-(dimethylamino)hexyl]-3-quinolinecarboxamide;
4-[[(3-Chloro-4-methoxyphenyl)methyl]amino]-6-cyano-N-[3-(4-morpholinyl)propyl]-3-quinolinecarboxamide;
4-[[(3-Chloro-4-methoxyphenyl)methyl]amino]-6-cyano-N-(phenylmethyl)-3-quinolinecarboxamide;
4-[[(3-Chloro-4-methoxyphenyl)methyl]amino]-6-cyano-N-(3-pyridinylmethyl)-3-quinolinecarboxamide;
4-[[(3-Chloro-4-methoxyphenyl)methyl]amino]-6-cyano-N-(2-pyridinylmethyl)-3-quinolinecarboxamide;
4-[[(3-chloro-4-methoxyphenyl)methyl]amino]-6-cyano-N-[2-(4-hydroxyphenyl)ethyl]-3-quinolinecarboxamide;
N-(1,3-Benzodioxol-5-ylmethyl)-4-[[(3-chloro-4-methoxyphenyl)methyl]amino]-6-cyano-3-quinolinecarboxamide;
4-[[(2,3-Dichlorophenyl)methyl]amino]-8-ethyl-3-(hydroxymethyl)-6-quinolinecarbonitrile;
4-[[(3-Chlorophenyl)methyl]amino]-8-ethyl-3-(hydroxymethyl)-6-quinolinecarbonitrile;
4-[[(4-methoxyphenyl)methyl]amino]-8-ethyl-3-(hydroxymethyl)-6-quinolinecarbonitrile;
3-(Aminomethyl)-4-[[(3-chloro-4-methoxyphenyl)methyl]amino]-6-quinolinecarbonitrile;
4-[[(3-Chloro-4-methoxyphenyl)methyl]amino]-3-[[(2-pyridinylmethyl)amino]methyl]-6-quinolinecarbonitrile;
4-[[(3-Chloro-4-methoxyphenyl)methyl]amino]-3-[(dipropylamino)methyl]-6-quinolinecarbonitrile;
3-[[Bis(2-methylpropyl)amino]methyl]-4-[[(3-chloro-4-methoxyphenyl)methyl]amino]-6-quinolinecarbonitrile;
2-Chloro-4-[[(3-chloro-4-methoxyphenyl)methyl]amino]-3-[(3-hydroxy-1-piperidinyl)methyl]-6-quinolinecarbonitrile;
4-[[(3-Chloro-4-methoxyphenyl)methyl]amino]-3-[(dimethylamino)methyl]-6-quinolinecarbonitrile;
4-[[(3-Chloro-4-methoxyphenyl)methyl]amino]-3-[(cyclohexylmethylamino)methyl]-6-quinolinecarbonitrile;
4-[[(3-Chloro-4-methoxyphenyl)methyl]amino]-3-[(cyclopentylmethylamino)methyl]-6-quinolinecarbonitrile;
4-[[(3-Chloro-4-methoxyphenyl)methyl]amino]-3-[[[(4-chlorophenyl)methyl]amino]methyl]-6-quinolinecarbonitrile;
4-[[(3-Chloro-4-methoxyphenyl)methyl]amino]-3-[[[(4-fluorophenyl)methyl]'amino]methyl]-6-quinolinecarbonitrile;
4-[[(3-Chloro-4-methoxyphenyl)methyl]amino]-3-[[[(4-methoxyphenyl)methyl]amino]methyl]-6-quinolinecarbonitrile;
4-[[(3-Chloro-4-methoxyphenyl)methyl]amino]-3-[[(phenylmethyl)amino]methyl]-6-quinolinecarbonitrile;
4-[[(3-Chloro-4-methoxyphenyl)methyl]amino]-3-[(cyclobutylamino)methyl]-6-quinolinecarbonitrile;
4-[[(3-Chloro-4-methoxyphenyl)methyl]amino]-3-[(cyclopentylamino)methyl]-6-quinolinecarbonitrile;
4-[[(3-Chloro-4-methoxyphenyl)methyl]amino]-3-[(cyclohexylamino)methyl]-6-quinolinecarbonitrile;
4-[[(3-Chloro-4-methoxyphenyl)methyl]amino]-3-[[(2-cyanoethyl)methylamino]methyl]-6-quinolinecarbonitrile;
4-[[(3-Chloro-4-methoxyphenyl)methyl]amino]-3-[[(2-hydroxyethyl)methylamino]methyl]-6-quinolinecarbonitrile;

4-[[(3-Chloro-4-methoxyphenyl)methyl]amino]-3-[[(2-hydroxyethyl)propylamino]methyl]-6-quinolinecarbonitrile;
4-[[(3-Chloro-4-methoxyphenyl)methyl]amino]-3-[[(1-methylethyl)amino]methyl]-6-quinolinecarbonitrile;
4-[[(3-Chloro-4-methoxyphenyl)methyl]amino]-3-[[(2-hydroxy-1-methylethyl)amino]methyl]-6-quinolinecarbonitrile;
4-[[(3-Chloro-4-methoxyphenyl)methyl]amino]-3-[[(1,3-dimethylbutyl)amino]methyl]-6-quinolinecarbonitrile;
4-[[(3-Chloro-4-methoxyphenyl)methyl]amino]-3-[[(1-ethylpropyl)amino]methyl]-6-quinolinecarbonitrile;
4-[[(3-Chloro-4-methoxyphenyl)methyl]amino]-3-[[(1-methylbutyl)amino]methyl]-6-quinolinecarbonitrile;
4-[[(3-Chloro-4-methoxyphenyl)methyl]amino]-3-[[(2,2,2-trifluoroethyl)amino]methyl]-6-quinolinecarbonitrile;
4-[[(3-Chloro-4-methoxyphenyl)methyl]amino]-3-[[(2,2-dimethylpropyl)amino]methyl]-6-quinolinecarbonitrile;
4-[[(3-Chloro-4-methoxyphenyl)methyl]amino]-3-[(ethylamino)methyl]-6-quinolinecarbonitrile;
4-[[(3-Chloro-4-methoxyphenyl)methyl]amino]-3-[[(2-methoxyethyl)amino]methyl]-6-quinolinecarbonitrile;
4-[[(3-Chloro-4-methoxyphenyl)methyl]amino]-3-[[(2-hydroxyethyl)amino]methyl]-6-quinolinecarbonitrile;
4-[[(3-Chloro-4-methoxyphenyl)methyl]amino]-3-[[(3,3-dimethylbutyl)amino]methyl]-6-quinolinecarbonitrile;
4-[[(3-Chloro-4-methoxyphenyl)methyl]amino]-3-[[(3-methylbutyl)amino]methyl]-6-quinolinecarbonitrile;
4-[[(3-Chloro-4-methoxyphenyl)methyl]amino]-3-[(propylamino)methyl]-6-quinolinecarbonitrile;
4-[[(3-Chloro-4-methoxyphenyl)methyl]amino]-3-[(ethylmethylamino)methyl]-6-quinolinecarbonitrile;
4-[[(3-Chloro-4-methoxyphenyl)methyl]amino]-3-[(diethylamino)methyl]-6-quinolinecarbonitrile;
4-[[(3-Chloro-4-methoxyphenyl)methyl]amino]-3-[(methylpropylamino)methyl]-6-quinolinecarbonitrile
4-[[(3-Chloro-4-methoxyphenyl)methyl]amino]-3-[[(2-cyanoethyl)amino]methyl]-6-quinolinecarbonitrile;
4-[[(3-Chloro-4-methoxyphenyl)methyl]amino]-3-[[methyl(2-methylpropyl)amino]methyl]-6-quinolinecarbonitrile;
4-[[(3-Chloro-4-methoxyphenyl)methyl]amino]-3-[[(2-ethoxyethyl)amino]methyl]-6-quinolinecarbonitrile;
4-[[(3-Chloro-4-methoxyphenyl)methyl]amino]-3-[[methyl(1-methylethyl)amino]methyl]-6-quinolinecarbonitrile;
4-[[(3-Chloro-4-methoxyphenyl)methyl]amino]-3-[[methyl(3-methylbutyl)amino]methyl]-6-quinolinecarbonitrile;
4-[[(3-Chloro-4-methoxyphenyl)methyl]amino]-3-[[[(1R)-1-methylpropyl]amino]methyl]-6-quinolinecarbonitrile;
4-[[(3-Chloro-4-methoxyphenyl)methyl]amino]-3-[[[[(2S)-tetrahydro-2-furanyl]methyl]amino]methyl]-6-quinolinecarbonitrile;
4-[[(3-Chloro-4-methoxyphenyl)methyl]amino]-3-[[(2-methoxyethyl)methylamino]methyl]-6-quinolinecarbonitrile;
4-[[(3-Chloro-4-methoxyphenyl)methyl]amino]-3-[[[[(2R)-tetrahydro-2-furanyl]methyl]amino]methyl]-6-quinolinecarbonitrile;
N-[[4-[[(3-Chloro-4-methoxyphenyl)methyl]amino]-6-cyano-3-quinolinyl]methyl]benzamide;
N-[[4-[[(3-Chloro-4-methoxyphenyl)methyl]amino]-6-cyano-3-quinolinyl]methyl]cyclohexanecarboxamide;
4-[[(3-Chloro-4-methoxyphenyl)methyl]amino]-6-cyano-N-(2-pyridinylmethyl)-3-quinolinepropanamide;
4-[[(3-Chloro-4-methoxyphenyl)methyl]amino]-6-cyano-3-quinolinepropanamide;
4-[[(3-Chloro-4-methoxyphenyl)methyl]amino]-6-cyano-N-ethyl-3-quinolinepropanamide;
4-[[(3-Chloro-4-methoxyphenyl)methyl]amino]-6-cyano-N-cyclohexyl-3-quinolinepropanamide; and
4-[[(3-Chloro-4-methoxyphenyl)methyl]amino]-6-cyano-N-cyclopentyl-3-quinolinepropanamide; and (ii) a pharmaceutically-acceptable salt thereof.

9. A compound according to claim 1, selected from:
(i) 4-[[(3-Chloro-4-methoxyphenyl)methyl]amino]-6-cyano-8-ethyl-N-(2-pyridinylmethyl)-3-quinolinecarboxamide; 4-[[(3-Chloro-4-methoxyphenyl)methyl]amino]-3-[[(3R)-3-hydroxy-1-pyrrolidinyl]methyl]-6-quinolinecarbonitrile; N-[[4-[[(3-Chloro-4-methoxyphenyl)methyl]amino]-6-cyano-3-quinolinyl]methyl]benzamide; N-[[4-[[(3-Chloro-4-methoxyphenyl)methyl]amino]-6-cyano-3-quinolinyl]methyl]cyclohexanecarboxamide; N-[[4-[[(3-Chloro-4-methoxyphenyl)methyl]amino]-6-cyano-3-quinolinyl]methyl]-2-pyridinecarboxamide 4-[[(3-Chloro-4-methoxyphenyl)methyl]amino]-8-ethyl-3-[(oxiranylmethoxy)methyl]-6-quinolinecarbonitrile; 4-[[(3-Chloro-4-methoxyphenyl)methyl]amino]-6-cyano-N-ethyl-3-quinolinepropanamide; 1-[3-[4-[[(3-Chloro-4-methoxyphenyl)methyl]amino]-6-cyano-3-quinolinyl]-1-oxopropyl]piperidine, trifluoroacetate; and 4-[[(3-Chloro-4-methoxyphenyl)methyl]amino]-6-cyano-N-cyclopentyl-3-quinolinepropanamide; and
(ii) a pharmaceutically-acceptable salt thereof.

10. A compound having the formula:

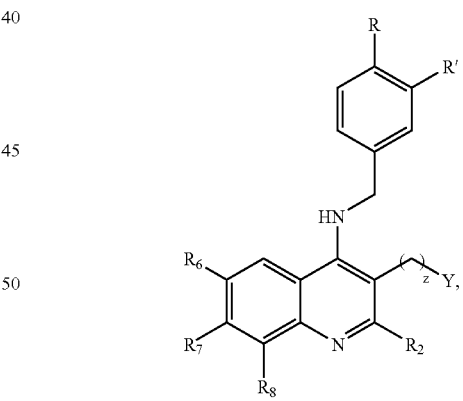

or a pharmaceutically-acceptable salt thereof, wherein:
R is —O($C_{1-4}$alkyl);
R' is halogen, $C_{1-4}$alkyl, $CF_3$, $OCF_3$, $OCHF_2$, O($C_{1-4}$alkyl) or S($C_{1-4}$alkyl);
$R_2$ is hydrogen or halogen;
Y is selected from —$NR_{10}R_{11}$, —(C=O)$NR_{10}R_{11}$, and —$NR_{10}$(C=O)$R_{12}$;
$R_6$ and $R_7$ are selected from hydrogen, halogen, $C_{1-4}$alkyl, trifluoromethyl, alkoxy, nitro, and cyano, $R_8$ is hydrogen, alkyl, substituted alkyl, or $CO_2$alkyl;

$R_{10}$, $R_{11}$, and $R_{12}$, are (i) independently selected from heterocyclo and heteroaryl; or (ii) taken together, wherein $R_{10}$ forms a three- to seven-membered heterocyclo ring with $R_{11}$ or $R_{12}$, or $R_{11}$ forms a three- to seven-membered heterocyclo ring with $R_{12}$; and z is 0, 1, 2, or 3.

11. A compound according to claim 10, or a pharmaceutically-acceptable salt thereof, in which R is $CH_3$ and R' is chloro.

12. A compound according to claim 11, or a pharmaceutically-acceptable salt thereof, in which:

$R_2$ is hydrogen or halogen;

$R_6$ is cyano;

$R_7$ is hydrogen; and $R_8$ is hydrogen, alkyl, or substituted alkyl.

13. A compound according to claim 10 having the formula:

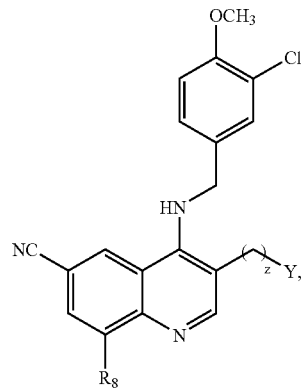

or a pharmaceutically-acceptable salt thereof.

14. A compound according to claim 13, or a pharmaceutically-acceptable salt thereof, wherein $R_8$ is hydrogen or $C_{1-4}$alkyl.

* * * * *

UNITED STATES PATENT AND TRADEMARK OFFICE
CERTIFICATE OF CORRECTION

PATENT NO. : 7,173,042 B2 Page 1 of 1
APPLICATION NO. : 11/018968
DATED : February 6, 2007
INVENTOR(S) : Yingzhi Bi et al.

It is certified that error appears in the above-identified patent and that said Letters Patent is hereby corrected as shown below:

In Claim 2, Column 83, line 17, please delete "teat" and insert -- are at --.

Signed and Sealed this

Tenth Day of April, 2007

JON W. DUDAS
*Director of the United States Patent and Trademark Office*

UNITED STATES PATENT AND TRADEMARK OFFICE
CERTIFICATE OF CORRECTION

PATENT NO. : 7,173,042 B2
APPLICATION NO. : 11/018968
DATED : February 6, 2007
INVENTOR(S) : Bi Yingzhi et al.

It is certified that error appears in the above-identified patent and that said Letters Patent is hereby corrected as shown below:

In Claim 2, Column 83, line 17, please delete "teat" and insert -- are at --.

Signed and Sealed this

Twenty-second Day of May, 2007

JON W. DUDAS
*Director of the United States Patent and Trademark Office*